US008151795B2

(12) United States Patent
Fishman et al.

(10) Patent No.: US 8,151,795 B2
(45) Date of Patent: Apr. 10, 2012

(54) METHOD OF DEMAND VALVE OXYGEN THERAPY FOR RAPID ABORT OF CLUSTER HEADACHE

(75) Inventors: Royce S. Fishman, Hernando, FL (US);
Peter L. Batcheller, Lake Ridge, VA (US); Michael Berger, Wildhaus (CH)

(73) Assignee: Linde AG (DE)

( * ) Notice: Subject to any disclaimer, the term of this patent is extended or adjusted under 35 U.S.C. 154(b) by 871 days.

(21) Appl. No.: 12/215,898

(22) Filed: Jun. 30, 2008

(65) Prior Publication Data

US 2009/0320845 A1  Dec. 31, 2009

(51) Int. Cl.
*A61M 16/00* (2006.01)
*A62B 7/04* (2006.01)
*F16K 31/26* (2006.01)

(52) U.S. Cl. ......... 128/204.26; 128/200.24; 128/204.18; 128/203.12; 128/898

(58) Field of Classification Search ............. 128/203.14, 128/204.18, 204.26, 203.12, 898
See application file for complete search history.

(56) References Cited

U.S. PATENT DOCUMENTS

| | | | |
|---|---|---|---|
| 5,787,882 A * | 8/1998 | Hamilton | 128/204.26 |
| 6,131,571 A | 10/2000 | Lampotang et al. | |
| 6,364,161 B1 * | 4/2002 | Pryor | 222/3 |
| 2005/0028823 A1 * | 2/2005 | Wood | 128/207.18 |
| 2006/0178354 A1 | 8/2006 | Lucas | |
| 2006/0201504 A1 | 9/2006 | Singhal et al. | |
| 2007/0014719 A1 | 1/2007 | Reading et al. | |

OTHER PUBLICATIONS

Balasubramaniam R, Klasser GD. "Trigeminal Autonomic Cephalagias: Part 1: Cluster Headache," *Oral Surg Oral Med Oral Pathol Oral Radiol Endod* 2007; 104:345-58.

Banken R. Agence D' Evaluation Des Technologies Et Des Modes D' Intervention en Sante. Provence de Quebec, Canada, May 2002.
Blau JN "Behaviour During a Cluster Headache," *Lancet* (Sep. 18, 1993) 342(8873):723-5.
Burns B, Watkins L, Goadsby PJ, "Treatment of Medically Intractable Cluster Headache by Occipital Nerve Stimulation: Long-Term Follow-Up of Eight Patients," *Lancet* (Mar. 31, 2007) 369(9567):1099-106.
Cohen AS, Matharu MS, Burns B[1], and Goadsby PJ, "Randomized Double-Blind, Placebo-Controlled Trial of High-Flow Inhaled Oxygen in Acute Cluster Headache," *International Headache Congress* 2007.
Burger EJ, Mead J., "Static Properties of Lungs After Oxygen Exposure," *J Appl Physiol* (Aug. 1969) 27(2):191-7.
Capobianco DJ, Dodick DW, "Diagnosis and Treatment of Cluster Headache," *Semin Neurol* 2006; 26: 242-259.
Comroe J.H., Dripps R.D., Jumke P.R., Deming M., "Oxygen Toxicity," *JAMA* Jul. 7, 1945, pp. 710-717.

(Continued)

*Primary Examiner* — Loan Thanh
*Assistant Examiner* — Kathryn D Sheikh
(74) *Attorney, Agent, or Firm* — Lerner, David, Littenberg, Krumholz & Mentlik, LLP

(57) ABSTRACT

Methods for easing the duration of pain experienced by patients during a cluster headache are disclosed including providing a high-pressure source of substantially pure oxygen, applying the oxygen to the patient so that inhalation by the patient is substantially limited to inhalation of the substantially pure oxygen, inhaling the substantially pure oxygen in order to cause hyperventilation by the patient, and continuing hyperventilation at least until the patient achieves respiratory alkalosis, hypocapnia hyperoxia, and until the pain is terminated. The method preferably includes using a demand valve having a predetermined manual purge flow rate and a variable output flow rate to the user based on respiratory demand.

37 Claims, 3 Drawing Sheets

Example of Single Severe Chronic Cluster Headache Sufferer Using the Invented Oxygen Demand Valve Method and a Random Approach to Breathing Using Demand Valve Without Specific Hyperventilation Or Other Steps In The Invented Demand Valve Method

OTHER PUBLICATIONS

Cohen AS, Manjit S., Matharu MS, Goadsby PJ. "Electrocardiographic Abnormalities in Patients With Cluster Headache on Verapamil Therapy," *Neurology* 2007 69: 668-675.

Kobari M, Meyer JS, Ichijo M, Kawamura J. Cortical and Subcortical Hyperfusion During Migraine and Cluster Headache Measured by Xe CT CBF. *Neuroradiology*. 1990. 32: 4-11.

Di Sabato F, Giacovazzo M, "Management of Cluster Headache in the Emergency Department," *J Headache Pain* Sep. 2005 6(4):294-7.

Dodick DW, Rozen TD, Goadsby PJ, Silberstein SD, Cluster Headache. *Cephalalgia* (Nov. 2000) 20(9):787-803.

Drummond PD, Anthony M, Extracranial Vascular Responses to Sublingual Nitroglycerin and Oxygen Inhalation in Cluster Headache Patients, *Headache* (Mar. 1985) 25(2):70-4.

Ekbom K, "Nitrolglycerin as a Provocative Agent in Cluster Headache," *Arch Neurol* (Nov. 1968) 19(5):487-93.

Ekbom K, "Treatment of Cluster Headache: Clinical Trials, Design and Results," *Cephalagia* 1995 Suppl. 15, 33-36.

Kudrow L Cluster Headache: Diagnosis and Management. *Headache* (Apr. 1979) 19(3):142-50.

Ekbom K, Hardebo JE. Cluster Headache: Aetiology, Diagnosis and Management. *Drugs* (2002) 62(1):61-9.

Favier I, Haan J, Ferrari MD, "Chronic Cluster Headache. A Review," *J Headache Pain* 2005 6:3-9.

Floyd TF. Clark JM, Gelfand R. Detre JA, Ratcliffe S, Guvakov D, Lambertsen CJ, Eckenhoff RG, "Independent Cerebral Vasoconstrictive Effects of Hyperoxia and Accompanying Arterial Hypocapnia at 1 ATA," *J Appl Physiol* (Dec. 2003) 95(6):2453-61.

Fogan L, "Treatment of Cluster Headache. A Double Blind Comparison of Oxygen vs Air Inhalation," *Arch Neurology* 1985: 42: 362-363.

Friedman AP, Mikropoulos HE, "Cluster Headaches," *Neurology* (Sep. 1958) 8(9):653-63.

Gregor N, Schlesiger C, Akova-Ozturk E, Kraemer C, Husstedt IW, Evers S, "Treatment of Cluster Headache Attacks With Less Than 6 mg Subcutaneous Sumatriptan," *Headache* (Sep. 2005) 45(8):1069-72).

Horton BT, "Histaminic Cephalgia: Differential Diagnosis and Treatment," *Proc Staff Meet Mayo Clin* May 30, 1956 31(11):325-33).

Kafer ER, "Pulmonary Oxygen Toxicity: A Review of the Evidence of Acute and Chronic Toxicity in Man," *Brit J Anaesthesia* 1971, 43, 687-695.

Kawamura J, Meyer JS, Terayma Y, Weathers S, "Cerebral Hyperemia During Spontaneous Cluster Headaches With Excessive Cerebral Vasoconstriction to Hyperoxia," *Headache* 1991 31: 222-227.

Kennealy JA, McLennan JE, Loudon RG, McLaurin RL, "Hyperventilation-Induced Cerebral Hypoxia," *Am Rev Respir Dis* (Sep. 1980) 122(3):407-12.

Kety SS, Schmidt CF, "The Effects of Active and Passive Hyperventilation on Cerebral Blood Flow, Cerebral Oxygen Consumption, Cardiac Output, and Blood Pressure of Normal Young Men," *J Clin Invest* (Jan. 1946) 25(1):107-19.

Kety SS, "Blood Flow and Metabolism of the Human Brain in Health and Disease," *Trans Stud Coll Physicians Phila* (Dec. 1950) 18(3):103-8.

Krozyck G, "Cerebral Vascular Reactivity Evaluation by Bold fMRI," *University of Toronto Medical Journal*, vol. 79, No. 1, Dec. 2001, 18-21.

Kudrow L, "Response of Cluster Headache Attacks to Oxygen Inhalation," *Headache* 21: 1-4, 1981.

Kunkle EC, "Clues in the Tempos of Cluster Headache," *Headache* (Jul. 1982) 22(4):158-61.

Loder E, Rizzoli P, McGeeney B, Ward T, Levin M, Shapiro RE, Tepper S, Newman L, Sheftell F, Rapoport A, Markley H, "Cluster Headache Treatment Dilemmas: The Experts Respond," *Current Pain and Headache Reports* 2007, 11:141-147.

Matharu MS, Boes CJ, Goadsby PJ, "Management of Trigeminal Autonomic Cephalagias and Hemocrania Continua," *Drugs* 2003; 63: 1637-1677.

Matta BF, Lam AM, Mayberg TS, "The Influence of Arterial Oxygenation on Cerebral Venous Oxygen Saturation During Hyperventilation." *Can J Anaesth* (Nov. 1994) 41(11):1041-6.

May A, Bahra A, Buchel C, Frackowiak RS, Goadsby PJ, "Hypothalamic Activation in Cluster Headache Attacks," *Lancet*, Jul. 25, 1998, 352 (9124):275-8).

May A, Ashbumer J, Buchel C, McGonigle DJ, Friston KJ, Frackowiak RS, Goadsby PJ, "Correlation Between Structural and Functional Changes in Brain in an Idiopathic Headache Syndromel," *Nat Med* (Jul. 1999) 5(7):836-8).

May A, "Cluster Headache: Pathogenesis, Diagnosis and Management," *Lancet* 2005: 366: 843-855.

May A, Leone M, Afra J, Linde M, Sandor PS, Eers S, Goadsby PJ, "EFNS (European Federation of Neurologial Societies) Guidelines on the Treatment of Cluster Headache and Other Trigeminal Autonomic Cephalagias," *European Journal of Neurology* 2006: 13: 1066-1077.

Nelson RF, "Cluster Migraine—An Unrecognized Common Entity," *Canadian Medical Association Journal*, Nov. 7, 1970, vol. 103, 1026-1030.

Nilsson Remahl AI, Ansjon R, Lind F, Waldenlind E, "Hyperbaric Oxygen Treatment of Active Cluster Headache: A Double-Blind Placebo-Controlled Cross-Over Study," *Cephalalgia* Nov. 2002 22(9):730-9.

Norris JW, Hachinski VC, Cooper PW, "Cerebral Blood Flow Changes in Cluster Headache," *Acta Neurol Scand* (Oct. 1976) 54(4):371-4.

Pascual J, Lainez MJA, Dodick D, Hering-Hanit R, Antiepileptic Drugs for the Treatment of Chronic and Episodic Cluster Headache: A Review, *Headache* 2007; 47:81-89.

Prescribing Information, Package Insert, Sumatriptan injection, Jan. 2006.

Prescribing Information, Package Insert, Zolmitriptan Nasal, Jan. 2007.

Rapoport AM, Mathew NT, Silberstein SD, Dodick D, Tepper SJ, Sheftell FD, Bigal ME, "Zolmitriptan Nasal Spray in the Acute Treatment of Cluster Headache: A Double Blind Study," *Neurology* 2007; 69; 821-826.

Rinow ME, Alan RS, "Effectiveness of a New Oxygen Demand Valve in Chronic Hypoxemia," *Chest* 1986. 90:2. 205-207.

Rozen TD, "New Treatments in Cluster Headache," *Current Neurology and Neuroscience Reports* 2002: 2: 114-121.

Rozen TD, "High Oxygen Flow Rates for Cluster Headache," Ltr to Editor Aug. 2004 *Neurology* 63, 593.

Rozen TD, "Cluster Headache: Diagnosis and Treatment," *Current Pain and Headache Reports* 2005, 9:135-140.

Sackner MA, Landa J, Hirsch J, Zapata A, "Pulmonary Effects of Oxygen Breathing. A 6-Hour Study in Normal Men," *Ann Intern Med* (Jan. 1975) 82(1):40-3.

Sakai F, Meyer JS, "Regional Cerebral Hemodynamics During Migraine and Cluster Headaches Measured by the Xe133 Inhalation Method," *Headache* 1978 18:122-132.

Sakai F and Meyer JS, "Abnormal Cerebrovascular Reactivity in Patients With Migraine and Cluster Headache," *Headache*. 1979 19: 257-266.

Sands GH, Letter to Editor, "Prescribing Oxygen for Cluster Headaches," *JAMA* Dec. 26, 1986, vol. 256, No. 24, 3349.

Smith DJ, Vane JR, "Effects of Oxygen Tension on Vascular and Other Smooth Muscle," *J Physiol* (Oct. 1966) 186(2):284-94.

Standley T, 2008, University of Cambridge, private communication to Linde Gas LLC, not yet published.

Tinits P. , "Oxygen Therapy and Oxygen Toxicity," *Annals of Emergency Medicine* 12:5, May 1983, 321-328.

US Naval Flight Surgeons Manual, Third Edition, 1991, Prepared by Naval Aerospace Medical Institute; Chapter 1, Physiology of Flight, 1-105.

Wood EH, Friedman AP, "Thermography in Cluster Headache," 4:107-11, 1976.

Biondi D, Mendes P. "Treatment of primary headache: cluster headache." In: Standards of care for headache diagnosis and treatment. Chicago (IL): National Headache Foundation; 2004. pp. 59-72.

Blue Cross Blue Shield Imitrex (subcutaneous sumatriptan injection) Utilization Management Criteria Policy, Blue Cross Blue Shield Web Site Jun. 2008.

Antonaci et at., The Effect of Hyperventilation in Cluster Headaches' Headache 31: 146-150, 1-38 Mar. 1991, p. 146,147.

International Search Report, PCT/US2009/03929, dated Aug. 13, 2009.

* cited by examiner

Figure 1: Results from Initial Phase of Pilot Study Comparing Time to Abort vs. Kip Pain Level for 15 Liters Per Minute Continuous Flow Using a Non Rebreathing Mask System vs. the Invented Oxygen Demand Valve Method Figure 2: Example of Single Severe Chronic Cluster Headache Sufferer Using the Invented Oxygen Demand Valve Method and a Random Approach to Breathing Using Demand Valve Without Specific Hyperventilation Or Other Steps in The Invented Demand Valve Method

METHOD OF DEMAND VALVE OXYGEN THERAPY FOR RAPID ABORT OF CLUSTER HEADACHE

FIELD OF THE INVENTION

The present invention relates to cluster headache therapy. More particularly, the present application relates to cluster headache therapy in which oxygen is inhaled by a patient in order to rapidly abort cluster headaches and to reduce re-attacks of cluster headaches.

BACKGROUND OF THE INVENTION

It is now well documented that cluster headaches are one of three primary headaches classified as trigeminal autonomic cephalagias.

Cluster headaches as defined by the 2004 International Headache Society Classification for Cluster Headache-II includes diagnostic criteria for cluster headaches as being (A) At least 5 attacks fulfilling the following criteria B-D, B) severe or very severe unilateral orbital, supraorbital, and/or temporal pain lasting 15-180 minutes if untreated, C) headache accompanied by at least one of the following i) ipsilateral conjunctival injection and/or lacrimation, ii) Ipsilateral nasal congestion and/or rhinorrhoea, iii) ipsilateral eyelid edema, iv) ipsilateral forehead and facial seating, and v) ipsilateral miosis and/or ptosis, C) a sense of restlessness and agitation, D) attacks having a frequency of 1 every other day to 8 per day and E) not attributed to any other disorder. Cluster headache sufferers are known to experience auras and shadows as do migraine sufferers, despite the 2 primary headache types being different in etiology (May A., Leone M., Afra J., Linde M., Sandor P. S., Eers S., Goadsby, P. J., EFNS (European Federation of Neurological Societies) "Guidelines On The Treatment Of Cluster Headache And Other Trigeminal Autonomic Cephalagias," *European Journal of Neurology* 2006; 13: 1066-1077).

Cluster headaches are sub-categorized into episodic and chronic conditions. The International Headache Society defines the episodic condition as attacks fulfilling criteria A-E for cluster headache and at least 2 cluster headaches lasting 7-365 days and separated by pain free remission periods of >1 month, and the chronic condition as attacks fulfilling criteria A-E for cluster headache and attacks recur over >1 year without remission periods or with remission period lasting <1 month.

Neither etiology nor pathogenesis of this disorder is known. Numerous investigations have attempted to help clarify these mechanisms (Kudrow L., "Cluster Headache: Diagnosis and Management," *Headache* (1979 April) 19(3): 142-50; May 2006). Cluster headache is a rare disorder with an estimated prevalence of 0.1% or less depending on the country (Matharu M. S., Boes C. J., Goadsby P. J., "Management Of Trigeminal Autonomic Cephalagias And Hemocrania Continua," *Drugs* 2003; 63:1637-1677). It is the most severe of the primary headaches and the most severe form of headache known to medicine. It is often called a "suicide headache" because those experiencing the repetitive higher level pain headaches often have thoughts of suicide, and, there are cases of sufferers committing suicide both during a cluster headache attack and during intervals between cluster headaches. The pain of cluster headache is often described in such graphic terms as boring in reference to drilling into, tearing or burning, and with such descriptive analogies as a "hot poker in the eye" or as if "the eye is being pushed out" (Capobianco D. J., Dodick D. W., "Diagnosis And Treatment Of Cluster Headache," *Semin Neurol* 2006; 26:242-269; Nelson, R. F., "Cluster Migraine—An Unrecognized Common Entity," *Canadian Medical Association Journal*, Nov. 7, 1970, Vol. 103, 1026-1030). Pacing, walking, sitting and rocking during the attack are activities which are considered pathognomonic of this disorder (Kudrow 1979). Approximately 93% of cluster headache sufferers report being restless during attacks resulting in behaviors such as pacing with the intense pain resulting in irrationality, violence and head banging (Blau, J. N., "Behaviour During A Cluster Headache," *Lancet* (Sep. 18, 1993) 342(8873):723-5). It is not uncommon for cluster headache sufferers to fall asleep in place immediately after a severe cluster headache even with abortive or preventative medication being taken due to total exhaustion from dealing with the attack. Cluster headache patients, depending on the number of headaches per day and level of pain, may have high absentee rates from work or have to go on disability.

While the literature states that cluster headache sufferers may have on average from 1-3 headaches per 24 hour period, it is not unknown for those who have the chronic form of the condition to suffer as many as 16 cluster headaches a day for extended periods of time.

Abortive, transitional and preventative drugs and surgical procedures are used to manage cluster headaches. Many abortive and all preventative agents are used off label for cluster headache therapy i.e. their use for cluster headache therapy is not authorized by their official prescribing information or the Regulatory authorities but is used on the physicians initiative based on their individual conclusions regarding safety and efficacy.

Neither the etiology or mechanism by which the abortive and preventative drugs work in cluster headache is fully understood. Notably, none of the preventative medicines used in cluster headache are given on the basis of proven theoretical background. Their use is purely based on empirical evidence. (May A., "Cluster Headache: Pathogenesis, Diagnosis And Management," *Lancet* 2005: 366: 843-855).

The goal of abortive therapy for cluster headache is fast, effective and consistent relief. Acute treatments of choice include 100% oxygen at 7 l/min to 15 l/min, Sumatriptan at 6 mg injected subcutaneously, zolmitriptan at 5 or 10 mg administered nasally and injectable dihydroergotamine. For the treatment of cluster headache attacks, oxygen (100%) with a flow of at least 7 l/min over 15 minutes and 6 mg of subcutaneous Sumatriptan are drugs of first choice (Ekbom K., Hardebo J. E., "Cluster Headache: Aetiology, Diagnosis And Management," *Drugs* (2002) 62(1):61-9; May 2006)

Transitional therapy is used to suppress headache while long term preventative therapy is introduced and titrated to an effective therapeutic dose. A number of drugs such as Prednisone have been used for this purpose.

Preventative agents include verapamil, lithium carbonate, valproic acid, methysergide, daily ergot and the anti epileptic drugs topiramate and gabapentin, each of which was originally developed for therapeutic use conditions other than cluster headache. In the prophylactic or preventative treatment, verapamil is a first option (Ekbom 2002, May 2006). Although cluster headache is clinically and diagnostically distinct from migraine, many of the same pharmacologic agents are used in their management.

It is also not uncommon for cluster headache sufferers with extreme pain to take opioids such as morphine.

The result is that cluster headache patients are often taking what may be called a pharmaceutical cocktail of therapies, which in the non-oxygen abortive triptans, preventatives and opioids can separately, let alone together, generate potential adverse effects, especially at the cluster headache dosing levels which often far exceed the on-label use recommendation for these drugs. An example is the commonly used abortive subcutaneously injected sumatriptan and the commonly used preventative drug verapamil that are taken by many patients and where each has potential adverse cardiac effects.

Destructive or invasive surgical interventions reported in the literature as therapy for cluster headache include application of glycerol to the trigeminal ganglion, radiofrequency rhizotomy of the trigeminal ganglion, gamma knife surgery to the trigeminal nerve, trigeminal tractotomy, trigeminal sensory nerve root section, surgical section of the nervus intermedius, combinations of nerve section decompression of the facial nerve, endoscopic spheno-palatine ganglion blockage with lidocaine and corticosteroids, and radiofrequency lesions of the pterygopalatine ganglion. The reported complications from such procedures include death, permanent neurological impairment, including corneal anesthesia which can lead to visual loss, anesthesia dolorosa, jaw deviation and cluster attacks switching sides after a unilateral lesion has been made. (Burns B., Watkins L., Goadsby P. J., "Treatment Of Medically Intractable Cluster Headache By Occipital Nerve Stimulation: Long-Term Follow-up Of Eight Patients," *Lancet* (Mar. 31, 2007) 369(9567):1099-106; Rozen T. D., "New Treatments In Cluster Headache," *Current Neurology and Neuroscience Reports*, 2002: 2: 114-121; Rozen T. D., "High oxygen Flow Rates For Cluster Headache," Ltr to Editor August 2004 *Neurology* 63, 593; May 2006; Pascual J., Lainez M. J. A., Dodick D., Hering-hanit R., "Antiepileptic Drugs For The Treatment Of Chronic And Episodic Cluster Headache: A Review," *Headache* 2007: 47:81-89; Rapoport A. M., Mathew N. T., Silberstein S. D., Dodick D., Tepper S. J., Sheftell F. D., Bigal M. E., "Zolmitriptan Nasal Spray In The Acute Treatment Of Cluster Headache: A Double Blind Study," *Neurology* 2007; 69; 821-826).

These surgical procedures, while sometimes providing some period of relief from cluster headache, or a reduced level of pain, are often employed incremental to some form of continued oxygen or other abortive and preventative therapy, either at the same or reduced need levels immediately after the procedure or for some time thereafter, where the cluster headache sufferer may be free of attacks prior to the attacks then resuming.

Even to a lay person it should appear obvious that an unmet medical need exists for a therapy that is both fully safe and highly efficacious and which can reduce the impact of cluster headaches on the sufferers physical and psychological quality of life.

While a general vascular theory once also prevailed regarding cluster headache, this has been superseded by recognition that neurovascular factors are more important (May 2005).

The hypothalamus is thought to play a key role in the cluster headache condition (May 2005). It has been suggested that the primary defects in cluster headache are located in regulating centers in the anterior hypothalamus. There are several observations to support such a hypothesis. Alterations in biological rhythms of hormone secretion have been recorded, notably regarding cortisol, prolactin and testosterone, both during active periods and in clinical remission. The pineal sleep hormone melatonin is a biological marker of hypothalamic function and the circadian system, and its secretion has also been shown to be altered in cluster headaches (Ekbom 2002). Recent findings by positron emission tomography of an increased blood flow indicate vasodilation during attacks in the hypothalamic grey area on the painful side (May A., Bahra A., Buchel C., Frackowiak R. S., Goadsby P. J., "Hypothalamic Activation In Cluster Headache Attacks," *Lancet*, Jul. 25, 1998, 352 (9124):275-8) and the structural changes in the same area (May A., Ashburner J., Buchel C., McGonigle D. J., Friston K. J., Frackowiak R. S., Goadsby P. J., "Correlation Between Structural And Functional Changes In Brain In An Idiopathic Headache Syndrome, *Nat Med* (1999 July) 5(7):836-8) lend further support to a central hypothalamic origin of the disease.

Magnetic resonance imaging angiographic studies and conventional carotid angiography have demonstrated a dilated intracranial segment of the internal carotid and ophthalmic arteries on the painful side during or outside attacks. This loss of vascular tone is believed to result from a defect in sympathetic peri vascular innervation. The same nerves run to the eye, giving rise to the miosis and ptosis seen during attacks (Ekbom 2002).

However, most now consider the attack to also be associated with local dilatation of the extracranial vessels in the regions supplied by branches of the external carotid artery. According to Friedman A. P., Mikropoulos H. E., "Cluster Headaches," *Neurology* (1958 September) 8(9):653-63 and Wood E. H., Friedman A. P., "Thermography In Cluster Headache," *Res. Clin. Stud. Headache* (1976) 4:107-111, this is suggested by the fact that during an attack one observes (1) a dilated temporal artery in some cases, (2) injection of conjunctiva and congestion of nasal mucosa, (3) local rise of skin temperature, (4) reduced ache on compression of the temporal artery and (5) a favorable response to vasoconstrictor agents. Horton (Horton B. T., "Histaminic Cephalgia: Differential Diagnosis and Treatment," *Proc Staff Meet Mayo Clin* May 30, 1965 31(11):325-33) had found that compression of the common carotid artery and sometimes the temporal artery frequently gave prompt relief in the first stages of an attack. Horton considered that the attacks arose through local dilatation of branches of the external carotid artery. Kunkle (Kunkle E. C., "Clues In The Tempos Of Cluster Headache," *Headache* (1982 July) 22(4):158-61) in a few patients, observed that the pain was eased during compression of the ipsilateral temporal artery Extracerebral Flow Index (EFI) is an index of skull, scalp, muscle and skin tissue flow or volume. Sakai F. and Meyer J. S., "Abnormal Cerebrovascular Reactivity In Patients With Migraine And Cluster Headache," *Headache*, 1979 19: 257-266, reported that in cluster headache patients tested during the headache interval when EFI values were increased (12.5+/%0.5%) indicating vasodilation, 100% oxygen inhalation caused a diffuse and excessive reduction of the EFI values (7+/−2%), indicating vasoconstriction. Friedman 1958 reported that most of the cluster headache causal theories seem to agree that we are dealing with periodic attacks of local dilatation of extracranial vessels in areas mainly supplied by the branches of the external carotid arteries. In support of the hypothesis of vasodilation are the distended temporal artery in some of the cases, the injection or even bloodshot appearance of the eye, the congestion of the nose, the local increase of the skin temperature, the occasional relief upon compression of the temporal or carotid artery and the usual good response to vasoconstrictive agents. Also in favor of the theory that dilation of extracranial vessels is responsible is the fact that since epinephrine does not constrict the intracranial vessels, the relief it gives in studies during such attacks must be due to the vasoconstriction of extracranial vessels. Friedman also referred to Kunkle 1982 who suggested that there is probably an increased susceptibility of the carotid artery of cluster headache patients to diverse vasodilating agents, and that this might be the reason for induced headache by histamine or alcohol. Drummond P. D., Anthony M., "Extracranial Vascular Responses To Sublingual Nitroglycerin And oxygen Inhalation In Cluster Headache Patients," *Headache* (1985 March) 25(2):70-4, found that extracranial blood vessels on the symptomatic side of cluster patients were particularly susceptible to the vasodilator effect of nitroglycerine and to the vasoconstrictor influence of oxygen.

The intense debilitating pain of a cluster headache is in part theorized to be caused by the dilation of blood vessels which in part creates pressure on the trigeminal nerve. Nitroglycerine, a potent vasodilator, is a pro drug for nitric oxide, which can activate the trigeminal vascular system. 1 mg of Nitroglycerine administered sublingually was used as a provocative agent in 38 males with cluster headache and an attack was elicited 100% of the time if the patient was tested during the course of a headache period (Ekbom K., "Nitroglycerin As A Provocative Agent In Cluster Headache," *Arch Neurol* (1968 November) 19(5):487-93). An increased sensitivity to vasodilator stimuli was therefore seen, and it was reported that attacks may be triggered by alcohol, histamine or nitroglycerine, with onset occurring after an interval of 30 to 50 minutes after intake. This time latency before an expected attack is of great interest as regards the underlying mechanisms. Nitroglycerin is a donor of nitric oxide and it was deemed tempting to believe that a local hypersensitivity to vascular effects of NO is one part of a chain of events that leads to a cluster headache attack following critical disturbances of the autonomic balance. Activation of the trigeminovascular system and cranial autonomic parasympathetic reflexes may explain the pain and the autonomic features of cluster headache (Ekbom 2002).

A number of observations have indicated that there is vasodilation of the ipsilateral ophthalmic artery during a cluster headache attack. These include increased corneal indentation, pulse amplitude, intraocular pressure and skin temperature around the eye, as well as decreased blood flow velocities on ultrasonography. Magnetic resonance angiography performed during spontaneous attacks of cluster headache revealed marked dilation of the ophthalmic artery ipsilateral to the pain (Capobianco 2006). In a study of 112 patients with cluster headache, Wood 1976 found that islands of hypothermia were in the medial supraorbital area supplied by extracranial branches of the internal carotid artery (ophthalmic terminations). Drummond 1985 reported that when 100% oxygen was administered through a plastic mask at the rate of 10 liters per minute for at least 10 minutes, it produced significantly greater reduction in supraorbital pulsations on the symptomatic side in patients with headaches. Decreases in both arterial territories following oxygen inhalation were significantly greater during cluster headache than between cluster headaches or than in control subjects. 15 of 16 cluster headache patients reported at least some relief after breathing 100% oxygen for 10 minutes, the headache subsiding almost completely in 12 patients after 15 minutes. Changes in pulse amplitude of the superficial temporal artery pulsations on the symptomatic side recorded after 10 minutes of oxygen inhalation indicated the amplitude decreased in 15 of the 16 patients studied and averaged 30%.

Clinical observations of cephalic vascular changes accompanying typical cluster headache attacks have been consistently reported (Ekbom 1975).

While oxygen is effective in aborting a cluster headache the mechanism of the effectiveness of oxygen in treating cluster headache is not understood and the percentage of cluster headache sufferers who experience successful oxygen therapy, especially chronic sufferers over the age of 50, leaves much room for improvement. Reductions in cerebral blood flow, cerebral vasoconstriction, activation of the descending inhibitory neurons from the brainstem and an abnormal chemo receptor sensitivity in cluster headache have been suggested. (May 2005)

Smith reported in 1966 that his results support the view that oxygen tension may play a major role in autoregulation of blood flow. (Smith D. J., Vane J. R., "Effects Of Oxygen Tension On Vascular And Other Smooth Muscle," *J Physiol* (1966 October) 186(2):284-94). Evidence for a direct vasoconstrictive effect of oxygen on cerebral blood vessels in vitro has been reported. As is well known and accepted by those versed in the art, Kety S. S. Schmidt C. F., "The Effects Of Active And Passive Hyperventilation On Cerebral Blood Flow, Cerebral Oxygen Consumption, Cardiac Output, And Blood Pressure Of Normal Young Men," *J Clin Invest* (1946 January) 25(1):107-19, showed that in young men there is a 59% increase in CBF in response to 5% carbon dioxide. Kety S. S., "Blood Flow And Metabolism Of The Human Brain In Health And Disease," *Trans Stud Coll Physicians* Phila (1950 December) 18(3):103-8, reported that the most remarkable observation in patients with cluster headache was the excessive cerebral and cranial vasomotor responsiveness to 100% oxygen inhalation during cluster headaches. In healthy young male volunteers, Kety had found using his method that 100% oxygen was reported to decrease cerebral blood flow, (hereinafter referred to as CBF) by approximately 13%. Norris J. W, Hachinski V. C., Cooper P. W., "Cerebral Blood Flow Changes In Cluster Headache," *Acta Neurol Scand* (1976 October) 54(4):371-4 reported increased CBF values in a patient during a cluster headache attack. Sakai F., Meyer J. S., "Regional Cerebral Hemodynamics During Migraine And Cluster Headaches Measured By The Xe133 Inhalation Method," *Headache* 1978 18:122-132, in an extensive study, presented CBF findings from contralateral and ipsilateral hemispheres. During the cluster attack there was a significant increase in CBF in the contralateral hemisphere even greater than that for the ipsilateral side. Later Sakai 1979 assessed cerebral vasomotor responsiveness using Xe 133 generated serial measurements of regional CBF during the steady state and during either 5% carbon dioxide inhalation, voluntary hyperventilation or 100% oxygen inhalation, also expressed as states of hypercapnia, hypocapnia or hyperoxia, in groups of patients with either migraine or cluster headache. Normal volunteers of both sexes showed a reduction of Fg, where Fg is CBF in gray brain matter, by 9.4+/−5.4%, correlating with Kety's earlier report. Sakai reported the cerebral vasoconstrictive response to 100% oxygen inhalation showed a diffuse and excessive reduction on the headache and non-headache side compared to normals and with migraineurs. The 100% oxygen inhalation also provided prompt and notable relief of headache. Precisely why an excessive cerebral vasoconstrictive response occurs during 100% oxygen breathing in patients with cluster headache, but not in migraine headache, is not fully understood. Differences in the disorder of cerebral vascular receptor sites in cluster headache and migraine headache is the suspected explanation. Apparently the effect of hyperoxia on catecholamine, serotonin, and possibly other vascular receptors, is excessive in patients with cluster headache. Apart from the direct oxygen effect on cerebral vessels influencing their neurotransmitter receptors, another possibility which may contribute to the resulting vasoconstriction is the Pasteur effect, whereby the cerebral tissue lactate levels vary inversely with the cerebral $PO_2$ levels, the higher the $PO_2$, the lower the tissue lactate and CBF. In summary, it has been show by these authors that increased $PO_2$ levels potentiated the constrictive effect of catecholamines and 5 hydroxytryptamine on skeletal muscle, which may account for the effect of 100% oxygen breathing on CBF.

Kobari M, Meyer J S, Ichijo M, Kawamura J., "Cortical and Subcortical Hyperfusion During Migraine and Cluster Headache Measured by Xe CT CBF," *Neuroradiology* 1990 32: 4-11, measuring CBF with high resolution color coded images produced by stable Xenon enhanced CT imaging, found that during cluster headache attacks, local CBF values are markedly increased bilaterally in all cerebral cortical and subcortical regions excluding the occipital cortex. Cerebral hyperperfusion during cluster headaches is observed in the same regions as seen in migraine headaches, but appeared to be greater in degree and more prominent ipsilateral to the head pain. Local CBF values for cerebral cortex, basal ganglia and white matter of both hemispheres were markedly increased during attacks of headache, exceeding those seen in migraine. They also tended to be greater on the side of the headache and associated with cephalic autonomic signs. The closer correlation between the side of the headache and local CBF increases suggested involvement of the trigeminal nerve in the occurrence of cerebral hyperfusion.

This was followed by Kawamura J., Meyer J. S., Terayma Y., Weathers S., "Cerebral Hyperemia During Spontaneous Cluster Headaches With Excessive Cerebral Vasoconstriction to Hyperoxia," *Headache* 1991 31: 222-227, measuring local cerebral blood flow in 3 dimensions using Xenon enhanced CT imaging during spontaneously occurring cluster headaches, during headache free intervals and immediately after terminating attacks by inhalation of 100% oxygen, found that CBF values for temporal cortex, basal ganglia and subcortical white matter were increased. Immediately after terminating attacks of cluster by 100% oxygen for five minutes, CBF values for temporal cortex and basal ganglia became significantly decreased below normal values in five patients with spontaneously occurring cluster headache. Prompt relief of head pain by inhalation of 100% oxygen was reported as associated with abolition of the hyper perfusion of both cortical and subcortical brain structures that occurs during spontaneously occurring cluster headaches and is followed by excessive cerebrovascular vasoconstriction. The conclusion reached was that rapid termination of head pain by hyperoxia associated with excessive cerebral vasoconstriction suggests that this vascular phenomenon is unique to cluster headaches and offers clues to its pathogenesis. The characteristic unilateral orbital and retro-orbital head pain is consistently ameliorated by digital compression of the carotid artery in the neck or 100% oxygen inhalation which is a potent cerebral vasoconstrictor.

In summary, it is accepted knowledge in the literature that as an abortive therapy for cluster headache, high levels of oxygen blood saturation lead to reduced cerebral hyperperfusion, high levels of cerebral vasoconstriction, reduce oxidative stress, and promote cellular respiration (Kawamura 1991; Cohen A. S., Matharu M. S., Burns B.[1], and Goadsby P. J., "Randomized Double-Blind, Placebo-Controlled Trial Of High-Flow Inhaled Oxygen In Acute Cluster Headache," *International Headache Congress* 2007), although the complete mechanism of the effectiveness of oxygen in treating cluster headache despite decades of literature is still not fully understood (Kudrow L. Response of Cluster Headache Attacks to Oxygen Inhalation. *Headache* 21: 1-4, 1981, May 2005).

It is important to state at this point that oxygen therapy as used to treat cluster headaches is not similar in mechanism or intended benefit to the use of oxygen in respiratory therapy. In traditional respiratory therapy, for example of Stage 3 or Stage 4 chronic obstructive pulmonary disease also known as COPD, the objective is long term, continuous and non stop oxygen therapy in order to raise oxygen saturation above a minimally required level in order to sustain life and, better yet, provide some semblance of an active vs. sedentary life for the outpatient or home care patient, and at a relatively normal respiration rate. The patient, especially in Stage 4 of COPD, is usually on continuous oxygen therapy 24 hours a day 7 days a week. A low arterial blood oxygen saturation of 88 out of a maximum value of 100 taken at rest versus a normal arterial blood oxygen saturation in the low to mid 90's is more or less a universally recognized requirement in order to qualify for reimbursement of oxygen based respiratory therapy.

In cluster headache therapy the primary objective of oxygen use is to saturate the blood and raise the oxygen level as close as possible to 100% in as short a time as possible, to cause cerebral vasoconstriction which it has been found results in the cluster headache being aborted. This can occur during symptoms just before or during an actual cluster headache. The cluster headache sufferer is not at rest nor breathing normally when using oxygen for therapy, but is hyperventilating from both the hyperactivity and the pain caused by a cluster headache. This also impacts the volume of oxygen consumed by a cluster headache sufferer vs. a patient who has COPD in late Stage 3 or 4 within the same time frame. Finally, while such a COPD patient tends to be on oxygen full time or near full time, a cluster headache sufferer only uses oxygen just before, at the start of or during a cluster headache. There are always intervals between cluster headaches, and, there may be long intervals between cluster headaches when the sufferer does need or use oxygen.

First cited by Horton in 1956, the use of oxygen therapy has since become the standard treatment in relieving headache attacks. 100% oxygen inhalation administered at a continuous flow rate of 7 to 12 l/min for 15-20 minutes with a non-rebreathing mask has been most cited as being effective in approximately 50% to 80%, but more commonly a cited figure of 70% of subjects, and often as being effective within 5 minutes, as first cited by Kudrow 1981 and Fogan L., "Treatment of Cluster Headache. A Double Blind Comparison of oxygen vs. Air Inhalation," *Arch Neurology* 1985: 42: 362-363, and then by Ekbom in 2002 (Ekbom K, Hardebo J E. Cluster Headache: Aetiology, Diagnosis And Management. Drugs (2002) 62(1):61-9). Importantly, there is no linking of the abort time to the severity of the cluster headache. Kudrow 1981 and Fogan 1985, as well as all virtually all textbook and other articles on cluster headache treatment instruct patients to use this method and the continuous flow rate range. The rationale behind this prescribed oxygen flow rate is unknown, but this has become doctrine since the Kudrow study (Rozen 2002). Additional references evidencing oxygen efficacy as an abortive agent for cluster headache include Ekbom K., "Treatment Of Cluster Headache: Clinical Trials, Design and Results," *Cephalagia* 1995 Suppl. 15, 33-36; Dodick D. W., Rozen T. D., Goadsby P. J., Silberstein S. D., "Cluster Headache," *Cephalalgia* (2000 November) 20(9):787-803; Rozen 2002, May 2006, Cohen A S, Matharu M S, Burns B[1], and Goadsby P J. "Randomized Double-Blind, Placebo-Controlled Trial Of High-Flow Inhaled Oxygen In Acute Cluster Headache" *International Headache Congress* 2007 and Balasubramaniam R., Klasser G. D., "Trigeminal Autonomic Cephalagias: Part 1: Cluster Headache," *Oral Surg Oral Med Oral Pathol Oral Radiol Endod* 2007; 104:345-58. It has been reported that subjects respond to higher flow rates of 15 l/min after not responding to traditionally used flow rates of 7 l/min. (Rozen 2004 letter to editor), and, the higher flow rates have been shown in controlled studies to be safe and effective (Cohen 2007). As recently as 2004, however, it was stated that there is no evidence that more than 15 l/min of continuous flow provides any incremental benefit in aborting a cluster headache (Rozen 2004). As suggested by this author in a private communication to the inventors, this perception is in large part generated due to Neurology and headache specialty training versus training received by a Pulmonologist regarding available oxygen delivery systems and methods and the multi decade accepted standard of care consisting of 7-15 l/min continuous flow non-rebreathing mask systems.

In some patients, oxygen is completely effective at aborting an attack if taken when the pain is at maximal intensity, whereas in others the attack is only delayed for minutes to hours rather then completely alleviated. (Rozen 2002). However, it has been reported by several authors (Kudrow 1981, Matharu 2003, Rozen 2002) that a cluster headache attack can recur shortly after discontinuation of oxygen even if there had been a complete abortive response. This is now commonly called a re-attack. Using the above method which has become the standard of care regarding use of oxygen to abort a cluster headache, up to 25% of patients note that oxygen simply delays the attack for minutes to hours rather then completely aborting it. (Matharu 2003)

Favier I., Haan J., Ferrari M. D., "Chronic Cluster Headache. A Review," *J Headache Pain* 2005 6:3-9, reported the success rate with oxygen using the above method is greater among patients with episodic rather than chronic cluster headache, with Kudrow 1981 previously reporting that 75% of patients obtained significant relief from cluster pain, with treatment success defined as complete or almost complete cessation of head pain within 15 minutes for at least 7 of 10 attacks, with the greatest benefit (92.9%) being found among episodic patients under 50 years of age and the least benefit (57%) being found among chronic patients over 49 years of age.

In summary, the consensus in the literature is that success of the treatment to abort a cluster headache with oxygen is related to high continuous flow rates of 7 liters to 15 l/min, high oxygen concentration desirably as close to 100% oxygen as possible, and allowing a reasonable amount of time for inhalation.

A major deficit in the existing literature on the use of oxygen to abort a cluster headache, is that efficacy and time to abort is given in terms of sex, age and other criteria, but no relationship is given between the level of a cluster headache in terms of pain, for example, using the Kip scale, which is broadly used to describe cluster headaches in the US patient community and to some degree in the medical community, and the efficacy of oxygen and time to abort. Solicited cluster headache sufferer input indicate that there is a direct correlation between Kip or pain level of a cluster headache and abort time when using oxygen. An added factor not always recorded or reported is when oxygen therapy was initiated, i.e., at the start of symptoms, after the start of an actual attack or well into the attack.

Several sources of oxygen exist that may be used to generate the continuous flow l/min rates described in the literature and representing the current standard of care for aborting a cluster headache with oxygen. The most common source of continuous oxygen flow is an oxygen regulator with a flow meter control that is attached to a compressed gas cylinder of medical oxygen. Liquid oxygen (LOX) reservoirs are used in some European countries. However, only a few models have possible flow rates as high as 15 l/min and can only provide this flow rate for a limited period of time. Portable LOX units use heated manifolds to convert LOX to oxygen gas. The heated manifold LOX to gas conversion capacity is related to manifold size and for portability battery size and weight relative to power consumption required to generate the needed manifold heating. Due to LOX system cost and typical reimbursement policies, cluster headache sufferers may have only one portable LOX unit which is usable for perhaps aborting 1-2 cluster headaches that they need to keep refilling at home from a reservoir. However, they can have multiple compressed gas cylinders of various sizes, including those considered carryable or portable, which provide flexibility and sufficient oxygen for numerous cluster headache attacks. Oxygen concentrators are rarely used due to their typically low continuous flow volumes of 5 l/min or less, with some more expensive systems providing 10-15 l/min. In addition, oxygen concentrators only generate 93% mole percent oxygen when a source of 100% oxygen is most desirable for effective cluster headache therapy.

The devices historically tried and used to delivery continuous flow oxygen inhalation to the cluster headache sufferer primarily include disposable nasal cannula, low to medium oxygen concentration oxygen masks and non-rebreathing high oxygen concentration mask systems with one way valves on the mask itself and a 1 liter reservoir bag. It is important to emphasize that these 3 oxygen delivery systems were and are produced and intended for use in respiratory therapy for COPD and other pulmonary ailments, and not for cluster headache therapy, for which they have been adopted.

In respiratory therapy applications, patients use relatively low continuous flow rates with <3 l/min being typical, in the course of normal sedentary or walking respiration where supplemental oxygen is required. As COPD increases in severity, the patient usually leads an increasingly sedentary lifestyle even though some degree of exercise is encouraged, and requires more oxygen in the form of a higher continuous flow rate, but is still breathing at a relatively normal rate in terms of breaths per minute. As evidenced by the upper continuous flow limit of 15 l/min of just a few LOX systems and oxygen concentrators but most providing a much lower maximum flow rate, higher continuous flow rates are not used in outpatient or homecare self administered respiratory therapy.

Nasal cannula and low to medium concentration oxygen masks result in a high degree of dilution of delivered oxygen with air, such that actual inhalation of anywhere at or near 100% oxygen is impossible. These are no longer prescribed by physicians or used by cluster headache sufferers either schooled in the art, aware of the literature or participating in patient organization support groups.

As broadly noted in the US and European medical literature, a continuous flow non-rebreathing mask with a 1 liter reservoir bag is the standard of care delivery device for abortive oxygen therapy. When using such a non-rebreathing mask system, key factors in achieving adequate cluster headache therapy include continuous flow oxygen rate, mask volume, reservoir bag volume, ventilatory resistance and tightness of mask fit. These are all variables in delivering at or near 100% oxygen.

Traditional non-rebreathing masks systems, originally designed for respiratory therapy, use a head strap to hold the mask on the patients head. This is because of the extended periods of use, which can be 24 hours a day and 7 days a week for late Stage 3 or Stage 4 COPD patients. A tight facemask seal is not always needed or achievable due to slippage or stretching of the elastic band head strap on disposable non-rebreathing masks systems worn for such extended periods of time. Because the typical non-rebreathing mask system is disposable and intended for respiratory therapy use where patients generally use a head strap the one way valves on these masks are made of non durable thin rubber, plastic, vinyl or silicone. They are about the size of a nickel coin, with the thickness of a business card, and are mounted on the mask over a pattern of small holes. The design is supposed to allow exhaled gases to escape, but not allow air to enter. The reliance on a head strap to hold the mask in place by respiratory therapy patients leaves the mask itself relatively unflexed and the valves intact and functional, whereas cluster headache patients typically grabbing the mask to hold it as tight as possible against their face and flexing the mask by doing so can lift or pop the valves off the mask surface exposing the holes in the mask beneath the valve leading to air entering the mask and diluting incoming oxygen from its source during every inhalation.

In the US, it is not common practice among cluster headache sufferers to use a head strap to hold a non-breathing mask in place for three reasons. First, the elastic head strap touches a sensitive part of the head during a cluster headache which is an important factor as many cluster headache sufferers experience skin surface allodynia during an attack. Second, the mask with just the head strap does not provide a tight enough facial seal to assure minimization of room air leaking into the mask. Cluster headache sufferers therefore tend to hold the mask tightly against their faces to create a tight seal and maximize the oxygen concentration being delivered. They also hold the mask itself tightly and roughly due to the intense pain being experienced and physical activity during a cluster headache attack, such as pacing back and forth or rocking back and forth while sitting. The mask is thus highly flexed and the valves may pop off or be partially gripped or torn off the mask, leading to a high degree of dilution of the continuous flow oxygen input into the mask with room air during inspiration. Finally, many cluster headache sufferers fall asleep from exhaustion immediately after an attack is over. They are advised by experienced cluster headache sufferers not to use a head strap but to hold the mask, so that if they fall asleep after an attack is over they are not at risk of having a non-breathing mask system over their nose and mouth if the oxygen cylinder it is attached runs out of oxygen while they are asleep.

The dose of oxygen the patient receives with a standard non-breathing mask with a reservoir bag is controlled by the rate of flow entering the mask circuit, which is mechanically controlled by a compressed gas regulator and its flow meter setting. Cluster headache sufferers tend to hyperventilate during the initial phase of a cluster headache due to pain, with hyperventilation increasing as the pain level and related physical activity, such as pacing, increases. Whether a cluster headache sufferer breathes normally, moderately fast or hyperventilates, the rate of oxygen flow into the mask remains the same. It is quite easy for anyone to self demonstrate using such a non-rebreathing mask that if one slowly hyperventilates at 30 breaths per minute or fast hyperventilates at 60 breaths per minute at 7 l/min continuous flow the reservoir bag collapses. It barely stays inflated if one increases the continuous flow input to 15 l/min.

This lack of sufficient incoming oxygen flow contributes to carbon dioxide accumulation in the mask from exhaled breath prior to the next breath, which leads to an unacceptable amount of carbon dioxide mixing with the oxygen entering the mask from its source. Carbon dioxide is well known to be a potent vasodilator in even small concentrations, such as 5-6%. Indeed, even a minute increase of about 0.25% alveolar carbon dioxide will lead to a 100% increase in pulmonary ventilation rate (*U.S. Navy Flight Surgeon's* Manual, 1991). MRI imaging studies using noninvasive continuous arterial spin-labeled-perfusion MRI have shown that 6% carbon dioxide in oxygen can substantially counteract the vasoconstrictive effects of the 94% oxygen in an inhaled mixture and reference the fact that breathing 100% $O_2$ at 1 atmosphere absolute (ATA) is known to be associated with a decrease in CBF (Floyd 2003). The effect of carbon dioxide is also supported by functional MRI imaging using BOLD or blood oxygen level dependent pulse sequences whereby it was reported that carbon dioxide increases the cerebral blood volume and cerebral blood flow within the brain by bringing about the vasodilation of arterioles and small arteries. And, in young men there is a 59% increase in CBF in response to 5% carbon dioxide (Krozyck G., "Cerebral Vascular Reactivity Evaluation by Bold fMRI," *University of Toronto Medical Journal*, Vol 79, number 1, December 2001, 18-21).

These flow rate levels vs. the breathing rate plus inspiratory oxygen volumes required by the cluster headache sufferer in the lead up to and during a cluster headache also result in considerable ventilatory inspiratory resistance, as the cluster headache sufferer is trying to inhale a volume of gas that is not available in the non-breathing mask due to its sole source of oxygen being the fixed continuous flow rate entering the mask from the oxygen gas source. The difficulty in inhaling from the non-rebreathing mask system that is not sufficiently or completely filled between the breaths of someone hyperventilating due to pain and physical activity leads to increased anxiety and further and or prolonged hyperventilation. The cluster headache sufferer can be gasping for breath trying to inhale volumes of oxygen or gas not available within the non-rebreathing mask system due to the fixed input continuous flow from the oxygen source. The result is that the cluster headache sufferer may be sucking in air through faulty portions of the masks facial seal by sheer negative pressure generated by inhaling, if not gasping, when no gas volume is left in the mask, or, lifting the mask to inhale room air out of panic in their mental state during a severe cluster headache. In either case, the result is a lowering of the blood oxygen saturation level that breathing 100% oxygen is supposed to achieve in order to generate an abortive therapeutic benefit and a defeat of the essential basis of the therapy.

The collapse of non-mask system reservoir bags when using 7 l/min is evidenced in published video studies of cluster headache attacks because the incoming oxygen volume has been exceeded by the inhalation rate of breath and volume per breath demand. The result is the patient inhaling a concentration of exhaled carbon dioxide along with new incoming oxygen from the continuous flow source, and, any air that leaks in through the mask facial seal due to negative pressure generated by the cluster headache sufferer gasping, decreasing the effectiveness of what would have been 100% oxygen, and therefore greatly diminishing the effectiveness of the therapy.

In summary, a hyperventilating and physically active cluster headache sufferer during an attack can require and be attempting to inhale high flow rates and volumes of oxygen that cannot be met by the standard of care fixed continuous flow rates of 7-15 l/min using a non-rebreathing mask with valves and a 1 liter reservoir bag. All of the above is an example of how the historical and current standard of care use for cluster headache therapy of 7-15 l/min continuous flow with a standard non-breathing bag designed for respiratory use creates a severely problematic therapy regimen for aborting a cluster headache and doing so in as little a time as possible.

In light of the above aspects of the use of a non-breathing bag, Tinits P., "Oxygen Therapy and Oxygen Toxicity," *Annals of Emergency Medicine* 12:5, May 1983, 321-328, cited that a non-rebreathing reservoir mask has been reported to deliver an FiO2 of about 90% at 8 to 15 l/min in respiratory therapy patients. A recent study by Standley in 2007 (Standley T, 2008, University of Cambridge, private communication to Linde Gas LLC, not yet published), measured oxygen present in a standard non-rebreathing mask and FiO2 over an initial period of approximately 3 minutes with a normal breathing rate. A continuous oxygen flow rate into the mask of 6 l/min resulted in an oxygen concentration in the mask system that was between 30 and 40%, for 9 l/min was between 40% and 50%, at 12 l/min was between mid 40 and 60% and at 15 l/min was between 50 and 60%. FiO2 clearly increased with increased flow rate but was also far below the 100% oxygen being fed into the mask from a source. Therefore, even a "high concentration non-rebreathing masks system," supposedly intended to deliver close to an ideal 93% from an oxygen concentrator or 100% oxygen from a compressed cylinder or liquid oxygen reservoir source, significantly fails to do so. This is critical regarding the level of efficacy achieved with such masks in treating cluster headache with what is supposed to be 100% oxygen inhaled. Despite the above data concerning the less than 100% oxygen actually inhalable versus what is fed into the non-rebreathing mask, the literature broadly indicates that 7-15 l/min of oxygen flow into the mask is still effective in aborting cluster headache in the range of 70% of patients studied. Just as important relative to cluster headache use of a non-rebreathing mask system, this same study revealed that during hyperventilation with a standard non-rebreathing mask, the percent oxygen actually in the mask ranged from the high 30% to mid 70% range, with normal ventilation it ranges from the low 50% to low 80% range, and, with hypoventilation it ranges from the low 50% to high 80% range. Where it would be desirable in the case of a cluster headache attack for hyperventilation to result in rapid escalation of oxygen levels in the blood, less far less then 100% oxygen would actually be delivered using such a standard non-rebreathing masks system . . . which is the standard of care oxygen delivery device today for cluster headaches. While a mouthpiece was suggested in the study to be superior, use of a mouthpiece and the application of nose clips to prevent the dilution with air inhaled via the nose is difficult for many cluster headache sufferers at the start of an attack, and, the nose clips can generate claustrophobia/anxiety during an attack. In summary, it would appear that the assumptions in the past as to the efficacy of 100% oxygen being inhaled via a non-rebreathing mask were in fact false as while 100% oxygen was being fed into the mask less if not far less than 100% oxygen was actually being inhaled.

Therefore, while all of the literature assumes because 100% oxygen is being delivered into a non-breathing mask and that is what the patient is inhaling, it is in reality not the case, in particular when hyperventilation is involved which cluster headache sufferers routinely do but on a randomized basis while breathing oxygen during an attack. Despite this, oxygen has been proven to have value as an abortive agent.

A medical demand valve for oxygen delivery is traditionally a resuscitation device for use in acute emergency medicine that delivers oxygen via full face mask and is not a device historically used for repetitive therapy of a specific chronic condition and specifically not for any primary headache condition.

A medical demand valve for oxygen is similar in mechanical function to a SCUBA diver's regulator that delivers air or another mixed gas only as of the point in time when the user starts to inhale, i.e., it is not a continuous flow system. A SCUBA diver's regulator delivers air or special mixtures including but not limited to oxygen plus another gas such as helium or nitrogen intended to safely support life under water at various depths. A medical oxygen resuscitation demand valve is intended for use only with oxygen and out of the water. Several mechanical differences exist between medical demand valves for oxygen resuscitation delivery and SCUBA demand such as but not limited to the medical oxygen demand valve requiring a lower pressure on inspiration to activate the demand valve diaphragm, and a lower expiration pressure.

A medical oxygen demand valve delivers oxygen to the user as soon as they try to inhale from an attached mask or mouth tube. As the user starts to inhale the slight drop in pressure within the mouth piece or mask lifts a valve and starts the oxygen flow. If the user inhales more deeply, more oxygen will flow in response to the increased demand, hence the name demand valve. When using a medical oxygen demand valve, oxygen dosage is controlled by the respiration rate and tidal volume of the individual patient. Demand valves are connected directly to a high pressure source of oxygen such as a compressed gas cylinder of medical oxygen, which has a regulator with a 40-60 psi output connection.

A typical medical oxygen demand valve for resuscitation operates on 40-60 psi pressure and delivers from 140 to 160 l/min maximum rate of flow, depending on the vendor. This is substantially different from continuous flow non-rebreathing masks where the oxygen flow rate is controlled by (i) the flow meter on an oxygen source which in the case of compressed gas cylinders and available medical oxygen flow meters is a maximum of either 15 or 25 l/min; (ii) the maximum 15 l/min at 22 psi from just a critical few portable liquid oxygen sources for limited durations of time before the manifold freezes; and (iii) a maximum of 10 l/min sometimes up to about 30 psi but usually at a much lower psi depending on vendor concentrator model that also delivers only about 93% oxygen which for cluster headache therapy is neither desirable nor as effective as a 100% oxygen source.

The use of a medical oxygen demand valve making available up to 140 to 160 l/min for cluster headache oxygen therapy and therefore amply providing for even fast hyperventilation which would consume less than half that rate is not a current standard of practice. As previously noted, it has been reported that higher oxygen flow rates above 15 l/min have not been shown to benefit cluster headache patients refractory to standard oxygen therapy. (Rozen 2004) This is in part due to the lack of familiarity that physicians who treat cluster headache patients have concerning demand valve oxygen delivery equipment, and, their reliance on the known standard of care, i.e., the non-rebreathing oxygen mask system, as the device by which they evaluate higher flow rates which are continuous in nature, fixed by the rate of flow delivered by the available flow meters, and which suffer from the other non-rebreathing mask related deficits described herein. Therefore, the use of a demand valve and its ability if used according to a specific method to significantly improve oxygen therapy of cluster headache is novel and not intuitive to anyone schooled in the art of cluster headache therapy. In fact, oxygen demand valves have been available for decades and have never been cited in the large base of historical cluster headache literature as a potential device for oxygen therapy in cluster headache.

Applicants are personally aware of a handful of cluster headache sufferers using demand valves. In these cases, as far as applicants are aware, the use of a demand valve was not prescribed by the patients physician, the unit was directly purchased by the patient in used or new condition from an internet source, and is used (i) wholly for convenience, as it reduces preparation time for use of oxygen when a cluster headache starts; (ii) eliminates the need to continuously buy disposable non-rebreathing masks with reservoir bags; and, (iii) because they are believed to make it easier to breathe during a cluster headache because of the very high oxygen flow rates available versus a fixed and much lower continuous flow rate available from standard medical oxygen flow meters. Importantly, applicants are not aware that these users employed any specific method of use of the demand valve that significantly improves efficacy by reducing the abort time for a cluster headache or generates other benefits such as reduced re-attacks, reduced number of cluster headache attacks in general or reduced need for other abortives such as sumatriptan. They generally breathe using the demand valve with no particular method or pattern other then their respiratory rate and inhalation volume needs being met during a cluster headache generated by pain, hyperactivity and anxiety.

Although hyperbaric oxygen has been much discussed as a therapeutic option and success has been reported, in what is regarded as a definitive placebo controlled double blind crossover study in patients within episodic and chronic disease no significant prophylactic effect was obtained. (Nilsson Remahl A I, Ansjon R., Lind F., Waldenlind E.: "Hyperbaric oxygen Treatment Of Active Cluster Headache: A Double-Blind Placebo-Controlled Cross-Over Study," *Cephalalgia* November 2002 22(9):730-9). Furthermore, hyperbaric oxygen therapy is not a practical form of abortive therapy since cluster headache sufferers have their headaches at home, at work, while shopping or otherwise located and need immediate access to therapy in order to achieve optimum relief. The scarcity and cost of use of hyperbaric oxygen systems at medical care facilities, the need for professional care givers specially trained in hyperbaric medicine to be present in order to operate them, the time it takes to get a patient into one, and, their high cost of use without reimbursement for cluster headache therapy, renders them also all but unusable for aborting a cluster headache.

No medical journal articles were found which discussed the use of an oxygen medical demand valve intended for emergency resuscitation use as a delivery device for cluster headache, nor therefore any specifically effective method of demand valve use. Three papers discussed demand valves in the context of those types of devices that provide small bolus doses of oxygen at points of inspiration equivalent to a relatively low continuous flow rate for respiratory therapy of COPD. An example of one of these papers is Rinow M. E., Alan R. S., "Effectiveness Of A New Oxygen Demand Valve In Chronic Hypoxemia," *Chest* 1986. 90:2. 205-207, which describes an inspiratory demand valve that attaches to an oxygen source and delivers oxygen after the sensor detects a negative pressure through a standard nasal cannula. It describes the intended use as being for patients having chronic hypoxemia secondary to COPD and in the case of this paper is based on studying patients under resting conditions, and not conditions of hyperventilation. The objective of using the type of demand valve described in this paper, now known as a conserver and intended for low flow rates such as 3 l/min, is an efficacy equivalent to non stop continuous flow and savings on use and cost of oxygen, and not a significantly improved efficacy or change in the change in the basic nature of the condition.

In summary, no mention of a medical demand valve originally designed for acute emergency resuscitation as being used to deliver oxygen for cluster headache therapy was found in the medical literature, and no reference was found in the literature to a specific method of demand valve use that provides the significant benefits described in this application.

In addition to oxygen, the leading pharmaceuticals used as abortive therapies for cluster headache include subcutaneous injection sumatriptan, inhaled zolmitriptan and injected dihydroergotamine, with subcutaneous injection sumatriptan being the dominant current abortive.

Patients with chronic cluster headache respond well to the use of subcutaneous sumatriptan, but to a lesser extent than episodic patients. Chronic cluster headache patients responded more slowly than patients with episodic cluster headache (Favier 2005).

In double blind, placebo controlled trails, the HT1b/D agonist sumatriptan (6 mg injected subcutaneously) was effective in about 75% of all cluster headache patients in terms of being pain free in 20 minutes Sumatriptan injection appeared to be 8% less effective in chronic cluster than in episodic cluster (Rozen 2002). The recommended dose of subcutaneously injected sumatriptan according to its authorized package insert is 6 mg, with a maximum of 2 doses per 24 hours. It is also stated that subcutaneously injected sumatriptan should not be given to patients with history, symptoms, or signs of ischemic cardiac, cerebrovascular, or peripheral vascular syndromes, significant underlying cardiovascular diseases, ischemic cardiac syndromes such as angina pectoris of any type, all forms of myocardial infarction and silent myocardial ischemic. Cerebrovascular syndromes include, but are not limited to, strokes of any type as well as transient ischemic attacks, and, there is a risk of myocardial ischemia and/or infarction. Although generally well tolerated, sumatriptan is contraindicated in patients with ischemic heart disease or uncontrolled hypertension. Caution must be exercised since cluster headache predominates in middle aged males who often have risk factors for cardiovascular disease, particularly tobacco abuse, which is present in up to 88% of cluster headache sufferers (Capobianco 2006). There is also some percentage of cluster headache sufferers who are needle phobic and for whom constant subcutaneous injections of sumatriptan are difficult if not impossible to pursue.

Chronic cluster headache sufferers in particular sometimes have many more than 2 cluster headache attacks a day. The result is that if they follow the package insert recommendations, only two of their daily cluster headaches can be treated with injectable sumatriptan. It is therefore not uncommon for in particular chronic extreme cluster headache sufferers to take more than the recommended daily dosage of Sumatriptan injection. The high cost of Sumatriptan is reportedly in the range of $125 to $175 per 2 doses. This presents a clear economic burden on cluster headache patients, especially given episodic sufferers may have attacks every day during an episode that can last for weeks or chronic sufferers may have attacks every day during a given year. Adding to this economic burden on the patient, is the fact that many insurers only provide coverage for up to 8 doses a month if they cover the use of the drug at all (Imitrex (subcutaneous sumatriptan injection) Utilization Management Criteria, Blue Cross Blue Shield North Carolina Web Site June 2008). It is well known to those familiar with the cluster headache sufferer community that they have learned to open and adapt the standard 6 mg injector drug carpule and use it for 2 doses of 3 mg each in order to extend the number of doses available and/or reduce their costs for the drug. It has been reported based on study results that use of 2 mg or 3 mg of subcutaneously injected sumatriptan is highly efficacious if used concomitantly with oxygen, with 3 mg injectable sumatriptan plus oxygen generating 74% efficacy with fewer side effects then the 6 mgm dose of Sumatriptan alone (Gregor N., Schlesiger C., Akova-Ozturk E., Kraemer C., Husstedt I. W., Evers S. "Treatment of Cluster Headache Attacks With Less Than 6 mg Subcutaneous Sumatriptan," *Headache* (2005 September) 45(8):1069-72). However, the remaining high cost for injectable sumatriptan on a constant basis, day after day during an episode or ongoing for a chronic sufferer, whether using 3 mg or 6 mg per cluster headache, with or without insurance and co-pay, is still prohibitively high. Just two headaches on average a day, every day for a year for a chronic cluster headache sufferer, treated alone with 6 mg of subcutaneously injected sumatriptan, and a high level co-pay of $30 per 2 daily doses, can generate an out of pocket cost to the patient of over $10,950. For a cluster headache sufferer who does not have co-pay coverage, or, is limited to only 8 doses covered by co-pay per month which is not an uncommon practice by insurance carriers, an impossible financial barrier is raised to routine use of the drug by cluster headache sufferers. Patients have also reported to the leading cluster headache patient organization that health insurance companies are starting to drop them as clients because of their routine use of expensive subcutaneous sumatriptan injections. Due to subcutaneous injectable sumatriptan currently being the lead abortive pharmaceutical for cluster headache and as noted in the literature and above its very high cost and limited insurance coverage, a means of significantly improving the efficacy of a solely oxygen based therapy of cluster headache due to its much lower cost is desirable from a health economics viewpoint, and, from a financial affordability viewpoint for the individual patient. Zolmitriptan nasal spray at doses of 5 and 10 mg is effective and tolerable for acute treatment of cluster headache (Rapoport 2007). Zolmitriptan nasal spray also has a recommended limit of 2 doses per day as stated in its authorized package insert. The prescribing information includes reference to possible drug interactions, effect of oral contraceptives on plasma concentrations, and recommends that it not be taken if the potential user has heart disease or a history of heart disease, have had a stroke or problems with blood circulation, have taken sumatriptan, rizatriptan, or ergotamines within the last 24 hours, have taken MAO inhibitors for depression within the last two weeks, Serotonin reuptake inhibitors such as Paroxetine, Fluoxetine or Sertraline, or serotinin neurepinephrine reuptake inhibitors such as Duloxetine.

The calcium channel blocker verapamil is a leading preventative pharmaceutical used off label for cluster headache. A daily dose of 240 to 320 mg of verapamil is the established preventative treatment of choice in the prophylaxis of chronic and episodic cluster headache (May 2005). If a patient needs greater than 480 mg/day of verapamil, then an electrocardiogram is necessary before each dosage change to guard against heart block. It is not uncommon for cluster patients to need dosages as high as 800 mg/day to gain cluster remission. (Rozen 2002). A recent study indicated that high dose verapamil is an increasingly common preventative treatment in cluster headache. Side effects include atrioventricular block and bradycardia, although their incidence in this population is not clear. The report strongly recommend EKG monitoring in all patients with cluster headache on verapamil. (Cohen A S, Matharu M S, and Goadsby P J. Electrocardiographic Abnormalities in Patients with Cluster Headache on Verapamil Therapy. *Neurology* 2007: 69: 668-675).

Cluster headache sufferers are therefore primarily faced with the use of subcutaneous sumatriptan or inhalable zolmitriptan, which are effective but can only be used a limited number of times a day without risk of adverse effects in particular to the heart, and is extremely costly, plus verapamil at dose levels which can also impact the heart.

In summary, patients want simple self-administered drugs with high efficacy, a tolerable, rapid and consistent action and low cost. Those patients who have more than two cluster headaches a day need an abortive agent that can be used to abort as many cluster headaches as they have per day. Sumatriptan is currently considered the abortive pharmacological agent of choice, but the recommended dose is only 2 per day and it is very expensive. Alternative acute treatments may be considered for patients with more than 2 attacks a day, patients with intolerable adverse effects or any contraindications to sumatriptan, and patients with extended periods of headache or a chronic syndrome. Very young or very old patients should also receive an individually tailored acute treatment. There is at present only limited experience in the management of patients in the latter age groups. It appears rational that pregnant and nursing women with a period of cluster headache should not be given sumatriptan. In most of the patients groups mentioned, inhalation of 100% oxygen is recommended as the acute therapy of use. (Ekbom 2002)

Oxygen inhalation is an effective method which can be safely used for the repetitive acute treatment of cluster headache. The great advantage with oxygen is that it has no established adverse effects and is much lower in cost then subcutaneous injection of sumatriptan (Ekbom 2002) or nasal zolmitriptan. Oxygen does not interact with and can be readily combined with other abortive and preventative medications and procedures. It can be used several times a day as opposed to injectable sumatriptan or inhaled zolmitriptan which can only be used up to a maximum of two times a day respectively. (Matharu 2003.) Inhaled oxygen can also provide an effective means of therapy for those cluster headache sufferers who are phobic regarding needles or self injection.

The cost per year for oxygen as an abortive for even a continuous chronic cluster headache sufferer is measured in a few thousand dollars versus the many ten's of thousands of dollars per year which subcutaneously injected sumatriptan or inhaled zolmitriptan can cost an insurance carrier or patient without insurance, or, a patient with a high co-pay, either for an episodic sufferer or in particular for a chronic sufferer. Should a method of oxygen use be identified that can significantly improve the efficacy of oxygen in aborting a cluster headache it would further enhance the use of this lower cost alternative to subcutaneously injected sumatriptan or inhaled zolmitriptan.

Accordingly, the need exists to provide a method of using oxygen which is relatively low in cost and affordable with or without insurance coverage by the majority of cluster headache sufferers, which can be safely used multiple times per day with no known adverse effects and which can provide an effective and significantly improved abortive method compared to existing standard of care continuous flow oxygen methods using a non-breathing bag system and which can reduce the need for sole or co-use of very high cost sumatriptan injection or inhaled zolmitriptan.

SUMMARY OF THE INVENTION

In accordance with the present invention, these and other objects have been realized by the invention of a method of easing the duration of pain experienced by a patient during a cluster headache comprising providing a high pressure source of substantially pure oxygen, applying the high pressure source of substantially pure oxygen to the patient in a manner such that inhalation by the patient is substantially limited to inhalation of the substantially pure oxygen, inhaling the substantially pure oxygen in a manner so as to cause hyperventilation by the patient, and continuing the hyperventilation at least until the patient achieves respiratory alkalosis, hypocapnia and hyperoxia until the pain is terminated. Preferably, the applying step comprises use of a demand valve having a predetermined manual surge flow rate, and a variable output flow rate to the user based on respiratory demands. In a preferred embodiment, the applying step further includes applying a facemask to the patient adapted to limit the inhalation to the substantially pure oxygen, or applying a mouthpiece to the patient that may require nose clips to the patient adapted to limit the inhalation to the substantially pure oxygen.

In accordance with one embodiment of the method of the present invention, inhaling of the substantially pure oxygen comprises the patient inhaling and exhaling substantially completely for at least three inhalations, and preferably for three to four inhalations.

In accordance with another embodiment of the method of the present invention, initiation of hyperventilation comprises rapidly hyperventilating at a rate of approximately 50 to 60 breaths per minute. Preferably, the continuing of the hyperventilation is carried out for from one to two minutes or until the patient feels the effects of hyperventilation, so as to achieve respiratory alkalosis, hypocapnia and hyperoxia as quickly as possible. In another embodiment, continuing of the hyperventilation further includes slowly hyperventilating at a rate of about 30 breaths per minute until the pain is completely terminated. In a preferred embodiment, the method further includes the patient continuing to breathe normally at a rate of 16-18 breaths per minute for a period of up to about 15 minutes based on how much time at this normal breathing rate is required to reduce or eliminate re-attacks in the individual patient. Preferably, if re-attacks occur, the method comprises continuing slowly hyperventilating at about 30 breaths per minute for at least one additional minute after complete termination of the pain, and subsequently slowing respiration to a normal rate of from 16 to 18 breaths per minute for a period of up to about 15 minutes. In another embodiment, the method includes continuing to breathe at the normal rate if re-attacks occur, for increasing periods of time of from about 16 to 30 minutes from the inhaling step, as needed to prevent or reduce further occurrences of re-attacks. In a preferred embodiment, the method of the present invention includes terminating the method after a maximum period of about 30 minutes from the inhaling step in order to breathe normal air for a minimum period of 15 minutes, and subsequently repeating the method.

In accordance with another embodiment of the method of the present invention, the method comprises terminating the method after an additional period of 1-15 minutes of normal breathing for a maximum total oxygen administration time of 30 minutes.

In accordance with another embodiment of the method of the present invention, if no end of pain is achieved within 20 minutes of starting oxygen administration, after a 5 minute period of no oxygen administration the method of the present invention described above should be repeated.

In accordance with another embodiment of the method of the present invention, the method includes subsequently slowing respiration to a normal rate of from about 16 to 18 breaths per minute for a period of up to about 15 minutes if the termination of pain takes place in less than about 10 minutes. In another embodiment, the method includes subsequently slowing respiration to a normal rate of from about 16 to 18 breaths per minute for a period of up to about 20 minutes if an additional re-attack occurs. In another embodiment, the method includes subsequently slowing respiration to a normal rate of from about 16 to 18 breaths per minute for a period of up to about 25 minutes if an additional re-attack occurs. In another embodiment, the method includes subsequently slowing respiration to a normal rate of from about 16 to 18 breaths per minute for a period of up to about 30 minutes if an additional re-attack occurs.

In accordance with another embodiment of the method of the present invention, the method includes subsequently slowing respiration to a normal rate of from about 16 to 18 breaths per minute for a period of up to about 20 minutes if complete termination of pain takes place in between 10 and 15 minutes. In another embodiment, the method includes subsequently slowing respiration to a normal rate of from about 16 to 18 breaths per minute for a period up to about 25 minutes if complete termination of the pain takes place in between 15 and 20 minutes. In another embodiment, the method includes subsequently slowing respiration to a normal rate of from about 16 to 18 breaths per minute for a period of up to about 30 minutes if complete termination of the pain takes place in between 20 and 25 minutes.

In accordance with another embodiment of the method of the present invention, the method is carried out repeatedly as many times as needed during a given day.

In accordance with another embodiment of the method of the present invention, the method is initiated at the first sign of a pending cluster headache. In another embodiment, the method is initiated after a cluster headache has fully begun. In another method the method is initiated just after the start of a cluster headache.

In accordance with another embodiment of the method of the present invention, the patient is an episodic or chronic cluster headache sufferer. Preferably, the patient is a chronic cluster headache sufferer over 50 years of age who may have cardiac problems and is not suffering from late Stage 3 or Stage 4 COPD and on supplemental continuous flow of oxygen therapy or a ventilator for purposes of respiratory therapy.

In accordance with another embodiment of the method of the present invention, the patient is a pregnant or nursing female, a child or elderly person.

In accordance with another embodiment of the method of the present invention, the cluster headache is of Kip 8 pain level or below, preferably whereby the abort time is reduced by about 50%.

In accordance with another embodiment of the method of the present invention, the method is repeated as needed.

In accordance with another embodiment of the method of the present invention, the method is carried out in conjunction with a cluster agent abortive medication, preferably sumitriptan, zoimitriptan, naritriptan, rizatriptan and dihydroergotamine. In another embodiment, the medication may comprise a transitional therapeutic comprising prednisone. In an additional embodiment, the medication may comprise a preventive therapeutic such as verapamil, valproic acid, topiramate, gabapentin, ergot-based medications, indomethicin, methysergide, prednisone or lithium. In another embodiment, the medication comprises an opioid comprising morphine.

In accordance with another embodiment of the method of the present invention, the method is carried out in conjunction with a surgical procedure intended as therapy for cluster headache.

In accordance with another embodiment of the method of the present invention, the method is carried out without the need for a co-abortive medication.

In accordance with another embodiment of the method of the present invention, it may, if carried out earlier enough during signs of an impending cluster headache or at the start of a cluster headache, abort said headache before it evolves into a runaway cluster headache that escalates to a Kip 9 or 10.

In accordance with another embodiment of the method of the present invention, the method is carried out in conjunction with the use of a pulse oximeter for monitoring oxygen saturation of the patient's blood.

In accordance with another embodiment of the method of the present invention, the method includes monitoring the patient's oxygen saturation using a pulse oximeter or the patient's saliva by pH testing so as to initiate the method based thereon.

In accordance with one embodiment of the method of the present invention, the demand valve accepts an input pressure from an oxygen source of from about 40 to 60 psi. In one embodiment, the demand valve provides a delivery pressure of about 60+/−5 cm of water. In another embodiment, the demand valve provides a flow rate demand mode of from 0 to 160 liters per minute. In another embodiment, the demand valve provides an inspiration valve crack pressure of from about 0 to −2 cm of water or less to start the inhalation of oxygen. In another embodiment, the demand valve provides an expiration resistance of about 3.8 cm of water or less at from about 11 to 70 liters per minute.

In another embodiment of the method of the present invention, the mask comprises a reusable resuscitation or disposable anesthesia mask with a tight facial seal and which can be held tightly against the face without damaging the integrity of the mask and facial seal, or a mouthpiece and nose clips to prevent the inhalation of any room air. In one embodiment, the method includes using a one-way T valve between the demand valve output port and the mask or mouthpiece.

In accordance with another embodiment of the method of the present invention, the high pressure source of substantially pure oxygen comprises a compressed gas cylinder of oxygen of from between 99.5 and 100% mole concentration oxygen. In another embodiment, the wall outlet high pressure source of substantially pure oxygen between 99.5 and 100% mole concentration located in a hospital, clinic, emergency room, ambulance or other medical care site supplied by a gaseous or liquid oxygen source supplying the building of an equal mole concentration range may be used. Preferably, the high pressure source of substantially pure oxygen is capable of providing to a delivery device an input pressure of about 50 psi and facilitating the delivery of a maximum flow rate of about 160 l/min.

In accordance with another embodiment of the method of the present invention, the method includes easing the pain experienced by a patient suffering from a cluster headache comprising providing a high pressure source of pure oxygen and a demand valve, inhaling the pure oxygen in a manner so as to cause hyperventilation by the patient, and changing the rate of the hyperventilation by the patient. In a preferred embodiment, the changing hyperventilation includes hyperventilation at a rate of about 50 to 60 breaths per minute and hyperventilation at a rate of about 30 breaths per minute.

In accordance with the present invention, a method of significantly reducing the duration of pain experienced during a cluster headache comprises a cluster headache sufferer inhaling by self administration 100% oxygen from a high pressure source using a medical demand valve administration system, such as those previously used for resuscitation, with required flow rate, inspiration and expiration activation pressures at the onset of cluster headache pain or symptoms. The method includes the cluster headache sufferer taking from 3 to 4 very deep breaths inhaling and exhaling as completely as possible, and then rapidly hyperventilating for 1 to 2 minutes at 50 to 60 breaths per minute, or until the patient feels the effects of hyperventilation, to achieve respiratory alkalosis, hypocapnia and hyperoxia as quickly as possible, and then slow hyperventilating at about 30 breaths per minute until the pain is completely ended.

In accordance with one embodiment of the method of the present invention, the individual optimizes the above method in order to achieve the most effective therapy for their own specific condition by (i) determining if continuing to breathe normally for less than a full therapy period of up to 15 minutes is deemed sufficient to reduce or eliminate re-attacks; or (ii) if re-attacks start to occur, extending their inhalation of oxygen at 30 breaths per minute for one additional minute after pain is completely ended and then slowing their respiration to a normal rate of about 16-18 breaths per minute for up to 15 minutes, while continuing to breathe at a normal rate to an end point of about 16-30 minutes from the start of therapy, ending at whichever point in time they determine that there has been an elimination or sufficient reduction in re-attacks for their individual condition, or (iii) if no abort is achieved within 30 minutes of continuous oxygen, discontinue oxygen for about a 15 minute period breathing normal air, again starting the demand valve therapy method of the present invention as described above.

In accordance with another embodiment of the present invention, the method of the invention (i) can reduce the abort time for a cluster headache of Kip 8 or below by approximately 50% or more; (ii) will prevent most of the runaway cluster headaches that escalate to a Kip 9 or 10 if started early unless there are other factors present or the cluster headache sufferer is asleep when the attack starts; (iii) can be used repeatedly as many times as needed in a given day; and (iv) should ideally start at the first sign of an impending cluster headache, but may also start after a cluster headache has fully begun, but desirably as early as possible after the onset of the cluster headache.

In accordance with another embodiment of the present invention, the method hereof is effective in general (i) within the population of episodic and chronic cluster headache sufferers, but is in particular safe and efficacious in such sufferers who are males over the age of 50 years of age and have a history of cardiac problems, making it superior to the standard of care oxygen therapy using a continuous flow non-breathing mask, and is potentially safer then the co-use of triptans with oxygen because the historical standard of care is insufficiently efficacious by itself, or the sole use of triptans, which puts patients with cardiac disease at risk and (ii) within the population of pregnant or nursing female sufferers and (iii) within the population of young or elderly sufferers in which it may be inadvisable to provide abortive triptans.

In accordance with another embodiment of the present invention, the method hereof is co-used with either injectable sumatriptan or inhaled zolmitriptan to achieve a rapid abort, where the co-use of oxygen reduces the dose required of either of the additional medications, or, may eliminate the need for said other medications.

In accordance with another embodiment of the present invention, a pulse oximeter is used during a cluster headache attack, and while using the method of the present invention to monitor and assure that a blood oxygen saturation of or as close as possible to 100% is being achieved at all times during the use of said method.

In accordance with another embodiment of the present invention, a pulse oximeter or pH testing of saliva is used on a routine basis during the day, and especially during known periods where a cluster headache sufferer is prone to attacks, where a drop in oxygen saturation or pH from the patients normal status can serve as a pre-warning of an impending cluster headache, allowing the implementation of this method of the present invention at a point in time prior to the onset of physical symptoms of an impending cluster headache or prior to the actual onset of the cluster headache itself, providing the ability to prepare for and use the method of the present invention just prior to or in the earliest stages of a cluster headache thereby further reducing the abort time.

BRIEF DESCRIPTION OF THE DRAWINGS

The present invention may be more fully appreciated with reference to the following detailed description, which in turn refers to the drawings in which.

DETAILED DESCRIPTION

Figure 1:
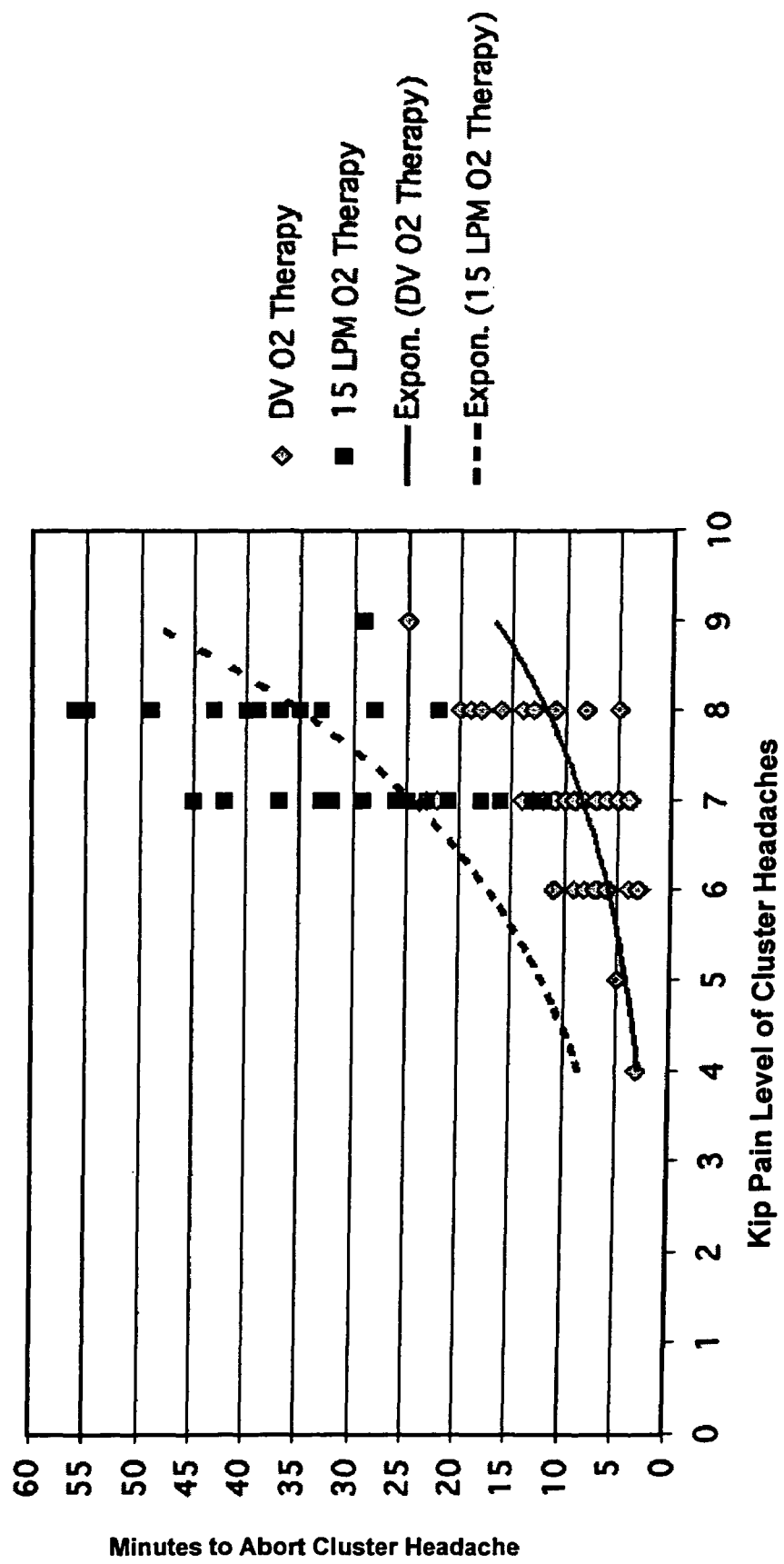
FIG. 1 is a graphical plot comparing the time to abort versus the Kip pain level for the continuous flow non-rebreathing system compared to the present invention.

As used herein, cluster headache is as defined by the 2004 International Headache Society Classification for Cluster Headache-II and as provided in the Background section of this application.

As used herein, "abort" is defined as the ending of pain during a cluster headache.

As used herein, a "re-attack" is defined as the re-occurrence of a cluster headache shortly after one has been aborted, or the re-occurrence of a cluster headache at a time interval less than the period between "normal" cluster headaches without any form of intervention. We differentiate a re-attack as a result of oxygen therapy from a rebound headache associated with the use of triptans such as injectable, nasal spray, and tablet forms of sumatriptan for the simple reason that we would all be in trouble if we developed a resistance to oxygen.

As used herein, the subjective and highly qualitative "Kip Scale", developed by a cluster headache sufferer, is defined as the scale by which cluster headache sufferers, particularly in the US, have for many years commonly graded their cluster headache pain levels, and, which has made its way into the literature. The Kip Pain Scale is defined by the following: Pain level 0 means no pain, pain level 1 means very minor, shadows come and go, pain level 2 means more persistent shadows, pain level 3 means shadows are getting constant but can deal with it, pain level 4 means the pain is starting to get bad and the cluster headache sufferer wants to be left alone, pain level 5 means the cluster headache is still not a "pacer" or the sufferer needing to walk back and forth, but they need their space, pain level 6 means the cluster headache sufferer wakes up wakes up grumbling and curses a bit but can get back to sleep without "dancing", pain level 7 means waking up, sleep is not an option, have to get up and pace or walk and finally falling into bed exhausted. Between pain level 6 and 7, the eye on the hit side starts to tear and the nose starts running. Pain level 8 is when it is time to scream, yell, curse, bang ones head with a fist or against a wall, rock back and forth or do whatever will work as an outlet for the pain, pain level 9 means the cluster headache sufferer starts to experience the "why me" syndrome, and level 10 means major pain, screaming, head banging, a trip to the emergency room and the cluster headache sufferer is depressed and suicidal. While this scale is not a standard accepted grading scale used in medical practice and clinical studies, its broad adoption by the U.S. cluster headache community of sufferers has led to its use in the medical literature in describing levels of cluster headache pain, and, it is referenced in this application.

As used herein the term "oxygen" is defined as the gas having an atomic number of 8 and an atomic weight of 15.999.

As used herein, "medical oxygen" and "100% oxygen" is defined as being 99.5 to 100 mole percent oxygen, which in the U.S. is officially designated Oxygen USP by the United States Pharmacopea, and whereby in the context of this invention, convention and availability in the marketplace is also sometimes referred to as 100 mole percent oxygen. Only a compressed gas cylinder of medical oxygen or a liquid oxygen reservoir or portable liquid oxygen unit can deliver medical oxygen that is 99.5 to 100 mole percent medical oxygen. A molecular sieve or pressure swing absorption based oxygen concentrator can generally only delivery 93 mole percent oxygen.

As used herein, the term "demand valve" is defined as a device historically used for emergency oxygen delivery and resuscitation, which delivers medical oxygen from a compressed gas source to a spontaneously breathing patient with minimal inhalation and expiration effort. Such medical demand valves require a source that can provide 40 to 60 psi medical oxygen, and the demand valve device preferably has a predetermined manual purge flow rate, and can deliver 140 to 160 liters per minute, and the rate of oxygen flow to the patient is a variable output flow rate which is controlled by the patients' own inspiratory requirements, and where the device addresses a broad range of respiratory rates from very low to very high, as in the case of a hyperventilating cluster headache sufferer.

As used herein, the term "non-breathing mask" is defined as a respiratory therapy oxygen delivery device consisting of a facemask generally having a section of small holes on each side of the mask covered by a small diameter and very thin valve of plastic, vinyl, silicone or similar material about the size of a nickel and the thickness of a business card, and a 1 liter reservoir bag that has long been adopted for use as the standard of care approach to cluster headache oxygen therapy. The valves are placed and intended to seal over the small holes on either side of the mask during inhalation, preventing air from entering the mask and facilitating the patient only breathing the contents in the mask and reservoir bag. When the user exhales, excess gas lifts the valve allowing it to escape. The primary gases in the non-rebreathing mask should be incoming medical oxygen, and, residual oxygen with exhaled carbon dioxide, other exhaled waste gases and moisture.

As used herein, "continuous flow" is defined as the continuous delivery of oxygen to a non-breathing mask measured in liters per minute where that flow rate is determined by the flow meter on the oxygen source such as a compressed gas cylinder or portable LOX system.

As used herein, "vasodilation" is defined as a widening of the lumen or opening of a blood vessel. Vasodilation is a major component of a cluster headache attack. Carbon dioxide and nitroglycerine are examples of vasodilators.

As used herein, "vasoconstriction" is defined as a narrowing of the lumen or opening of a blood vessel. Vasoconstriction results in a decrease in blood flow accompanied by an increase of the blood pressure, the degree of vasoconstriction being dependent on the causative agent. Oxygen, sumatriptan and zolmitriptan are examples of vasoconstrictors, and hypocapnia or hyperoxia are examples of causal mechanisms of vasoconstriction.

The present invention provides an improved method of aborting a cluster headache in terms of efficacy; e.g., reducing the time to abort. It has also demonstrated the capability to reduce re-attacks, as well as reducing the need for expensive co-abortive agents and, depending on the individual patient, potentially changing the nature of the cluster headache condition to a more benign pattern of attacks with reduced frequency and intensity. The present invention preferably includes the provision of 100% medical oxygen to a patient using a demand valve with the required pressure, flow rate, inspiration and expiration pressures, a facemask that will provide a tight hand held facial seal, or a mouthpiece and nose clips, and a method of use of the demand valve involving specific sequential periods of several different respiratory rates and manners of breathing.

In one embodiment of the present invention, there are four phases to the claimed demand valve administered oxygen therapy as a cluster headache abortive. These are (1) clearing nitrogen from the lungs, (2) fast hyperventilation, (3) slow hyperventilation and then (4) extended regular respiration for periods incremental to the time spent in Phase 1, 2 and 3 so as to bring the total continuous oxygen exposure aggregate time up to periods of 15, 20, 25, and 30 minutes, as needed to prevent re-attacks. It is critical that the cluster headache sufferer fully inhale and exhale as completely as possible during the first three phases of the method of the present invention, in order to insure more complete ventilation of the lungs during hyperventilation and the expelling of carbon dioxide, a vasodilative agent, as rapidly as possible. The four phases of the invented demand valve method are herein described in more detail.

In Phase 1, the clearing of nitrogen is accomplished by taking three to four very deep breaths of oxygen from the demand valve, exhaling and inhaling as completely as possible with each breath. At sea level pressure, Nitrogen is inert and makes up nearly 80% of the air we breathe. Clearing it from the lungs and replacing it with oxygen increases the partial pressure of oxygen in the lungs and arterial blood. Taking three to four very deep breaths of oxygen from the demand valve, exhaling and inhaling as completely as possible with each breath, starts the process of clearing the residual Nitrogen from the lungs and also starts the shift into hyperoxia, which can be defined as having more oxygen in the blood than normal. Phase 1 should ideally start at the first sign of an impending cluster headache, but may also start after a cluster headache has already begun, with the greatest effectiveness in terms of reducing abort time and therefore pain being related to how close prior to the start of or after the start of a cluster headache therapy is started.

In Phase 2, fast hyperventilation, which is a respiration rate of 50 to 60 breaths per minute, has the purpose of shifting the lungs and blood stream into respiratory alkalosis, hypocapnia, and hyperoxia as fast as possible. The transition from Phase 1 to Phase 2 is accomplished by simultaneously reducing the volume of oxygen inhaled while increasing the respiration to the rate range called for in Phase 2. This is not panting, but rather a tidal flow equal to a minimum of one liter of oxygen inhaled and exhaled each second. The cluster headache sufferer should maintain this rate of hyperventilation for a period of 1 to 2 minutes or until he or she clearly feels the effects of hyperventilation, such as dizziness, lightheadedness, or tingling in the hands or face. This is the most difficult phase of the therapy for most cluster headache sufferers. It is best to practice this phase prior to a cluster headache attack with the assistance of a coach or supporter to time the respiration rate.

In Phase 3, slow hyperventilation, which has a recommended respiration rate of 30 breaths per minute, the purpose is to maintain the benefits of hyperventilation, respiratory alkalosis, hypocapnia, and hyperoxia, but at a more comfortable respiration rate. The transition from Phase 2 to Phase 3 is accomplished by simultaneously increasing the volume of oxygen inhaled while decreasing the respiration rate to 30. This works out to an easy to remember respiration pattern of inhaling for one second and exhaling for one second with a minimum tidal flow equal to 1.5 liters of oxygen. The cluster headache sufferer should maintain this respiration rate until the cluster headache pain has clearly subsided. This phase is most effective in reducing the abort time by inhaling and exhaling as completely as possible while maintaining a respiration rate of 30. Phase 4 may be added as needed to enhance the prevention of re-attacks, which are common during the first month or which can occur later when just using the method of the present invention with Phases 1-3 above. Re-attacks tend to occur when the pain level is high, such as a Kip 7 or Kip 8, and the abort times are less than about 10 minutes in length. Although re-attacks are common with other forms of oxygen therapy, the theory behind re-attacks when using the method of the present invention during a pilot study has demonstrated a predictable and repeatable pathophysiology. This form of oxygen therapy is so effective in aborting the pain of a cluster headache attack in such a short period of time that insufficient time is spent in hyperoxia to abort the triggering mechanism. When the temporary physiological effects of inducing vasoconstriction with hyperventilation on 100% oxygen that include, but are not limited to: hyperoxia and respiratory alkalosis with its attendant hypocapnia and elevated arterial pH dissipate following cessation of the method of the present invention, and the triggering mechanism is still present, the cluster headache attack resumes. There were a few recorded instances in an initial pilot study using the method of the present invention where re-attacks occurred following aborts lasting about 15 minutes, but none where the total time of continuous oxygen therapy was greater than 20 to 25 minutes. Remaining in hyperoxia for up to 15 or 20 minutes while using the method of the present invention appears to be effective in preventing most re-attacks when they start to occur. It should also be noted that re-attacks are easily aborted with the method of the present invention. By extending use of the demand valve as indicated, it appears that the method of this invention is not only able to abort the pain of a cluster headache, but is also able to abort the triggering mechanism.

Administration time is the key differentiator. During the initial 10 days to two weeks of the pilot study of the method of the present invention, a higher incidence of re-attacks was seen where the pain of a cluster headache at Kip-6 to Kip-8 was completely aborted in less than 10 minutes only to have another attack 15 to 45 minutes later. By extending the use of oxygen after a successful abort, defined as the ending of pain, to a total of 20 minutes of continuous oxygen inhalation, the re-attacks were largely or totally eliminated. As the goal of the demand valve therapy is to stop or abort the pain, remaining in hyperoxia after the abort to bring the total time on 100% oxygen to 15 to 20 minutes at a normal respiration rate appears to be a reasonable solution to remain pain free until the next regularly scheduled cluster headache attacks that occur every 2 to 3 hours during peak or high cycle periods. The patient may also extend Phase 4 to a total time of 25 to 30 minutes if the individual finds that this extension of time breathing 100% oxygen significantly reduces or eliminates re-attacks.

However, if no abort or elimination of pain is achieved within 30 minutes of starting the method of the present invention, the cluster headache sufferer should stop the method of the present invention, and after a 15 minute period of no oxygen use breathing normal air, should start the method of the present invention over again if the pain has not subsided.

Unlike the use of sumatriptan or zolmitriptan as an abortive, which have recommended limits of 2 doses a day, the method of the present invention can be repeated as many times a day as required by ongoing cluster headaches, due to the well established safety of the use of oxygen within the parameters of use described by the method of the present invention.

The method of the present invention may be performed by the cluster headache sufferer at home, at work, or while traveling, and, may also be provided by a medical care giver such as, but not limited to, a nurse, physicians assistant, paramedic or physician to the cluster headache sufferer in the case of a Kip 9 or 10, where they may be incapacitated from the standpoint of firmly holding a mask on their face themselves.

The method of the present invention requires hyperventilation with 100% oxygen as well as rapid changes in the rate of hyperventilation, which only an oxygen resuscitation type of demand valve can provide, and whose flow rate demands far exceed the capabilities of standard compressed gas cylinder medical oxygen flow meters, LOX systems and non-rebreathing mask systems.

Hyperoxia and hypocapnia are independent respiratory conditions that result in the vasoconstriction of cerebrovascular structures. During hyperventilation with 100% oxygen in accordance with the method of the present invention, these two conditions combine to provide a greater level of vasoconstriction than the sum of the two individual vasoconstrictive conditions by hyper-oxygenating the blood flow to the brain. When applied as an abortive therapy within and generated by the method of the present invention for cluster headache sufferers, this demand valve method will result in safe and successful aborts with greater efficacy and shorter abort times than possible with presently prescribed standard of care recommendations for continuous flow oxygen therapy at 7 to 10 liters/minute using a non-breathing mask system. (Biondi D, Mendes P. Treatment of Primary Headache: Cluster Headache. In: *Standards of Care for Headache Diagnosis and Treatment*. Chicago (Ill.): *National Headache Foundation;* 2004. p. 59-72). Moreover, as indicated by the results of a pilot study using the method of the present invention, this method also produces improved efficacy and shorter abort times than made possible using what for the standard non-rebreathing mask is the high continuous flow rate of 15 liters/minute oxygen cited by Dr. Todd Rozen, MD in a study of patients at the Michigan Headache & Neurological Institute (MHNI). As a result of the MHNI study using non-rebreather masks and an oxygen flow rate of 15 L/min, Dr. Rozen concluded from his clinical observations that cluster headache patients should not be deemed refractory to oxygen therapy unless flow rates up to 15 l/min have been utilized. Each of the presented patients had tried oxygen several times at the 7-10 l/min flow rate and experienced no change in headache intensity. On the higher flow rate (15 l/min) the patients had complete or near-complete headache alleviation. (Rozen T D. High Oxygen Flow Rates for Cluster Headache. Ltr to Editor August 2004 *Neurology* 63, 593.)

Normally, arterial hemoglobin in an individual breathing air at sea level is 96 percent saturated. When breathing 100 percent oxygen at sea level pressure, the hemoglobin becomes 100 percent saturated, and additional oxygen goes into simple solution in the plasma. Inhalation of 100% oxygen should result in at least 1.5 cc of additional oxygen carried in the plasma over that dissolved when blood is equilibrated with room air (Comroe J. H., Dripps R. D., Jumke P. R., Deming M., "Oxygen Toxicity," *JAMA* Jul. 7, 1945, pp. 710-717).

In addition, the oxygen carrying capacity of the blood hemoglobin is also very sensitive to changes in blood pH, also known as the Bohr effect. At an oxygen tension of 60 mm Hg, for example, at a pH of 7.2, 7.4, and 7.6, the arterial oxygen saturation is observed to be 84, 89, and 94 percent, respectively. Carbon dioxide is the major determinant of blood pH. In venous blood $PCO_2$ is high; accordingly, the pH is low. In arterial blood, the $PCO_2$ is less, as a result of the diffusion of carbon dioxide into the alveoli. The arterial blood, therefore, has a higher pH and can carry more oxygen at a given alveolar $PO_2$ than would be possible without this change in pH. Elevating the pH through hyperventilation increases hemoglobin's affinity for oxygen. The total of additional oxygen so transported is 11 percent greater than normal. (U.S. Naval Flight Surgeon's Manual, Third Edition, 1991, Prepared by Naval Aerospace Medical Institute: p 1-16.) Hypocapnia, even at $PaCO_2$ of 30 mmHg, results in cerebral vasoconstriction that exceeds any vasoconstrictive effect of normobaric hyperoxia. (Matta B E, Lam A M, Mayberg T S., "The Influence of Arterial Oxygenation on Cerebral Venous Oxygen Saturation During Hyperventilation," *Canadian Journal of Anesthesia*, Vol 41, 1041-1046, 1994).

Acute respiratory alkalosis decreases CBF, increases the affinity of hemoglobin for oxygen, and can result in cerebral hypoxia (Kennealy J. A., McLennan J. E., Loudon R. G., McLaurin R. L., "Hyperventilation-Induced Cerebral Hypoxia," *Am Rev Respir Dis* (1980 September) 122(3):407-12. However, Matta 1994 concluded that hyperoxia during acute hyperventilation improves oxygen delivery to the brain as measured by increased cerebral venous oxygen content and saturation. Floyd T. F., Clark J. M., Gelfand R., Detre J. A., Ratcliffe S., Guvakov D., Lambertsen C. J., Eckenhoff R. G., "Independent Cerebral Vasoconstrictive Effects Of Hyperoxia And Accompanying Arterial Hypocapnia At 1 ATA," *J Appl Physiol* (2003 December) 95(6):2453-61, reported that the observed decrease in CBF while breathing 100% O2 at 1.0 ATA represents the combined effects of arterial hyperoxia and hypocapnia. Furthermore, he reported that his data supported the hypothesis that breathing oxygen at 1.0 ATA causes cerebral vasoconstriction independently of any vasoconstriction associated with the accompanying arterial hypocapnia, and, that gray matter cerebral vasculature is relatively more sensitive to the vasoconstrictive properties of hyperoxia and vasodilatory properties of hypercarbia over the ranges tested. Using a non invasive MRI imaging method to measure CBF to test the hypothesis that an increase in PaO2 while breathing O2 at 1.0 ATA decreases CBF independently of the accompanying fall in PaCO2, Floyd found that the transition from breathing air to 100% O2 at 1.0 ATA caused a decrease in CBF of 33%.

When one hyperventilates, one casts off Carbon Dioxide faster than the body generates it. This creates an imbalance, causing carbon dioxide at a higher concentration in the bloodstream to flow rapidly through the alveolar membrane and into the exhaled breath, where the concentration of carbon dioxide is much lower. A similar imbalance causes oxygen we inhale to flow through the alveolar membrane into the bloodstream. As blood passes through the small alveolar sacks within the lungs, hemoglobin in the red blood cells casts off carbon dioxide, and oxygen bonds rapidly to the hemoglobin. Oxygen also dissolves in the blood plasma. When we hyperventilate on 100% oxygen, we displace the normal 79% nitrogen in the lungs with oxygen and we also cast off more carbon dioxide than the body generates. This elevates the arterial pH and that enables the hemoglobin in blood cells to attract and hold up to 11% more oxygen. Therefore, by hyperventilating on 100% oxygen we can super-oxygenate arterial blood to significantly increase vasoconstriction of the cerebrovascular system. Hyperventilation reduces carbon dioxide levels in the bloodstream. It also elevates arterial pH. An elevated pH enables hemoglobin to carry 11% more oxygen to the brain. Therefore, hyperoxia, hypocapnia, and an elevated pH above 7.4, causes the arteries and capillaries in and around the trigeminal nerve to constrict back to their normal size, relieving pressure on the trigeminal nerve, and aborting the pain of a cluster headache attack.

There are three abortive effects made possible by using demand valve administered oxygen therapy as a cluster headache abortive. They are hyperoxia, hypocapnia, and a combination of hypocapnia and hyperoxia. Hypocapnia is the more powerful vasoconstrictor. Their combined abortive effect is faster acting in aborting cluster headache attacks than sumatriptan injections. The effects of hyperoxia on CBF were previously discussed. An elevated level of carbon dioxide above normal is called hypercapnia. Hypercapnia acts as a cerebrovascular dilator so higher levels of carbon dioxide would aggravate a cluster headache attack extending its duration and intensity. At rest, the normal respiration rate is 15 to 18 inhale-exhale respiration cycles per minute. With a breath tidal volume of one half liter, that works out to a flow rate of 7 to 9 liters per minute. Climbing stairs for a normal person might escalate this to a demand for about 12 liters per minute. As the level of carbon dioxide is the primary determinate of the respiration rate, the physical activity associated with the agony of a violent, high Kip level cluster headache attack could easily result in the generation of higher carbon dioxide levels that would demand a respiration rate higher than 7 to 9 liters per minute. Moreover, if the respiration rate is artificially constrained to 7 to 9 liters per minute by a non rebreather mask during a violent cluster headache attack, this constrained respiration rate would easily result in the build up of carbon dioxide levels that could limit or totally negate the cerebrovascular constrictor effects of hyperoxia making an abort of the attack impossible.

The method of the present invention for aborting cluster headaches calls for respiration rates much faster than this. In order to work effectively as a cluster headache abortive, the present invention calls for fast hyperventilation at a respiration rate of about 50 to 60 inhale-exhale cycles/minute. With a tidal volume of one liter, that equals an initial oxygen flow rate of about 50 to 60 liters per minute. This far exceeds the capabilities of compressed gas cylinder medical oxygen flow meters, which are commonly limited to 15 or 25 liters per minute, or portable LOX systems which operate at 15 liters per minute for limited periods of time and are generally designed for flow rates less than half that.

Continued hyperventilating at a rate of about 50 to 60 inhale-exhale cycles/minute for about 1 to 2 minutes is recommended until the cluster headache sufferer feels the effects of hyperventilation. At this point, the method of the present invention calls for the user to slow the respiration rate to 30 inhale-exhale cycles/minute. This is Slow Hyperventilation. The cluster headache sufferer must maintain this respiration rate until the pain of the cluster headache attack subsides. At this respiration rate, the tidal volume should be close to 1.5 liters, making the oxygen flow rate 45 liters per minute. Breathing at this rate is still considered hyperventilation.

Of critical importance, is that while it has been widely reported in the literature, for example, by Ekbom in 2004, that 50% to 80% of cluster headache patients receive some benefit from standard of care oxygen therapy, it had previously been reported by Kudrow in 1981 that the greatest benefit of 92.9% was found among episodic patients under 50 years of age and the least benefit of 57% was found among chronic patients over 49 years of age and that 78% of episodic patients responded favorably to standard of care oxygen therapy while only 68.4% of chronic patients had success (Favier 2005).

The method of the present invention has now been demonstrated in our pilot study as working 95% of the time with chronic patients in their 50's and 60's having cluster headaches of a Kip 8 pain level or below, in addition to substantially reducing their abort times vs. the standard of care continuous rebreathing masks at 15 liters per minute which is considered a high continuous rate of flow by the medical community, and, reduces their need for the co-abortive subcutaneously injected sumatriptan, which previous to using the present invention had been routinely used with their non-rebreathing mask and continuous flow oxygen, and, reduces the number of re-attacks and the number of primary cluster headaches per day after some period of use. Therefore, the method of the present invention not only provides successful therapy to a previous patient segment that was resistant to oxygen therapy success, but, it significantly improves the efficacy of oxygen therapy above the standard of care in those who were or are using same.

Therefore, in another embodiment, the method of the present invention will provide a significant success rate of aborting a cluster headache as found by the inventors in their pilot study to be 95% for cluster headaches below a Kip 8, and of reducing or eliminating re-attacks even among chronic patients who are well over 50 years old, which is a group that has historically had a much lower rate of success with oxygen being efficacious. It can therefore be postulated that the method of the present invention would be as successful, if not more successful, in aborting headaches and reducing abort times in episodic patients who have a much higher rate of success with traditional standard of care continuous flow non-breathing mask systems then do chronic patients over 50 years of age.

FIG. 1 illustrates results from the initial phase of the pilot study concerning the significant benefits of the method of the present invention for 2 of enrolled cluster headache sufferers aged 51 and 57. Both participants are long term smokers consuming about 1 pack of cigarettes a day. Both have been long term users of subcutaneously injected sumatriptan. One had a heart attack and the other has a pacemaker, and therefore continued major use of subcutaneously injected sumatriptan is either not advised or restricted to an absolute minimum.

As shown in FIG. 1, use of the method of the present invention dramatically reduced the abort times to significantly less than the abort times resulting from the use of the standard of care continuous flow non-breathing mask therapy, even at what is considered by those schooled in the art and by the literature to be a high continuous flow rate of 15 liters per minute of oxygen.

In the pilot study conducted by the inventors, with anecdotal input from the handful of existing cluster headache sufferers one of whom used a demand valve for convenience vs. improved efficacy, just breathing from a demand valve does not lead to significant benefits in terms of reduced abort times, reduced re-attacks or potential changes in the nature of the condition such as a reduced number of cluster headache attacks. It is the specific novel method of use discovered by the invention that makes a difference.

Figure 2:
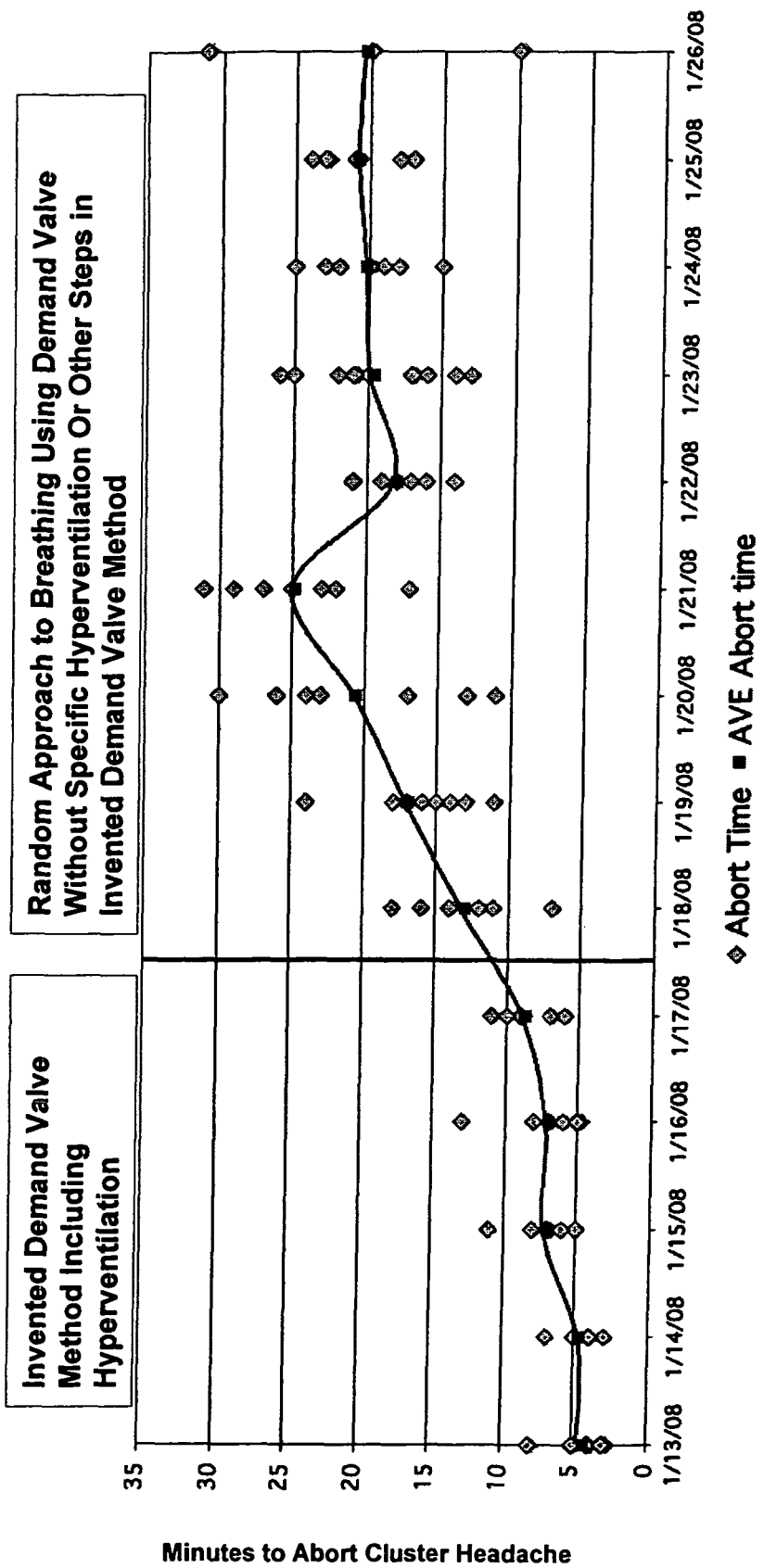
FIG. 2 is a graphical plot of time to abort for a chronic cluster headache sufferer using a random approach to breathing using a demand valve without a specific hyperventilation rate or timed sequence of breathing as compared to the method of the present invention.
Figure 3:
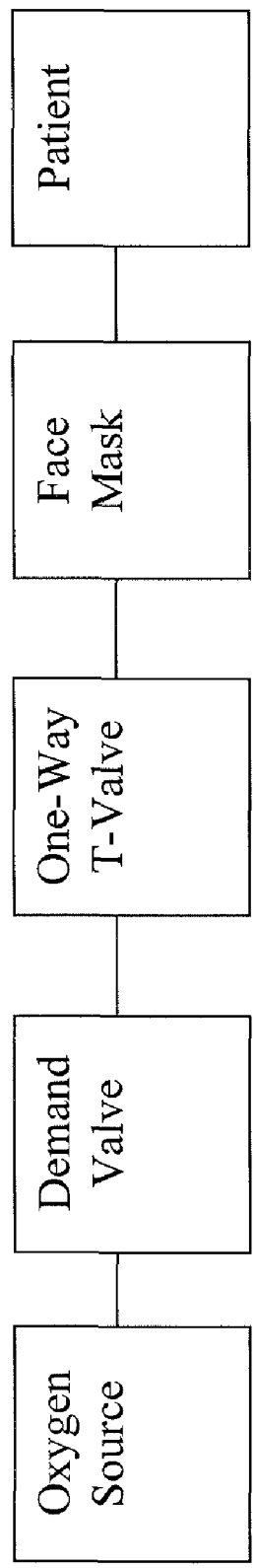
FIG. 3 is a schematic view of the elements useful in accordance with the present invention.

FIG. 2 illustrates data collected by one of the chronic cluster headache sufferers depicted in the pilot study results illustrated in FIG. 1. This study subject is 51 years of age and is very familiar with the procedures used in the method of the present invention. He executed these procedures to the letter for the first 5 of the 14 days illustrated in FIG. 2 with excellent results. At the end of the fifth day the study subject became concerned when the dizziness associated with the method of this invention persisted long after the abort and reoccurred spontaneously between attacks. Assuming this was due to the method of this invention, he consciously discontinued use of the method of the present invention for the next 9 days. He continued using the demand valve, but with more normal respiration rates that did not induce the dizziness associated with hyperventilation. During the 14-day data collection period, this pilot study subject suffered an average of 7.5 attacks a day/24 hrs with an average pain level of Kip-7.2/ attack.

The transition from using to not using the method of the present invention is clearly illustrated in FIG. 2 by a dramatic increase in average abort times, and, of equal importance, a marked increase in the variability of abort times the method of the present invention previously suppressed. A detailed follow up discussion with the study subject revealed the frequency and intensity of his attack had decreased significantly, but that the "dizzy spells" had continued to occur even when not using the demand valve or the method of the present invention. At that point a mutual decision was made to discontinue participation in the study, and promptly seek medical attention. The study subject was subsequently diagnosed with a Type II second-degree atrioventricular block, also called Mobitz Type II condition. This condition was not present during an earlier physical. Following a thorough clinical workup including an angiogram, the study subject was then fitted with a pacemaker and thereafter returned to use of the present invention.

In another embodiment, starting prior to or early at the onset of a cluster headache attack with the method of the present invention will prevent most of the runaway cluster headaches that escalate to a Kip 9 or 10 unless there are other factors present or the cluster headache sufferer is asleep when the attack starts.

In a further embodiment of the present invention, use of the method hereof may reduce the number and intensity of cluster headache attacks incrementally over time, and quite separate from re-attacks suffered by one with the condition, which is a change in the nature of the condition itself and is in particular a significant and novel benefit of the method of the present invention, but which will depend on the individuals physiology.

A further embodiment of the present invention involves the use by a cluster headache sufferer of a pulse oximeter that measures blood oxygen saturation if they, a family member or other care giver or observer are capable of using same and recording data during a cluster headache attack. The objective is to verify that they are achieving and maintaining a blood oxygen saturation level of or close to 100% during the therapy period of the method of the present invention. This will signify that they are performing the method hereof correctly, and, that they are getting the maximum potential benefit.

In another embodiment of the present invention, this invention may be used with other abortive pharmaceuticals as a co-agent or co-agents such as, but not limited to, available forms of sumatriptan, nasal zolmitriptan, naritiptan, rizatriptan or dihydroergotamine and or with transitional pharmaceuticals including, but not limited to, prednisone and or preventative pharmaceuticals such as, but not limited to, verapamil, valproic acid, topiramate, gabapentin, ergot based products, indomethicin, methysergide, prednisone or lithium and or opioids such as, but not limited to, morphine and or surgical therapy procedures intended to reduce or alleviate the cluster headache condition for some period of time.

In a further embodiment of the present invention, the cluster headache sufferer may use a pulse oximeter and or pH testing of saliva on a routine basis upon rising, mid day and prior to going to sleep, and, especially during known periods during the day, where, based on experience, the cluster headache sufferer is prone to attacks, and where a drop in oxygen saturation or pH from the patients normal status can serve as a pre-warning of an impending cluster headache, allowing implementation of the method of the present invention at a point in time prior to the onset of physical symptoms of an impending cluster headache or prior to the actual onset of the cluster headache itself, providing the ability to prepare for and use the method hereof just prior to or in the earliest stages of a cluster headache, thereby further reducing the abort time, and perhaps reducing the likelihood that a headache that would have been a Kip 9 or 10 is aborted before the pain reaches that level.

In a further embodiment of the present invention, dependent on the individual, the method hereof may reduce or eliminate the need for abortive, prophylactic or opioid co-medication by a cluster headache sufferer and in some cases, depending on the individual and Kip level of the cluster headache, provide faster relief than use of subcutaneously injected sumatriptan, thereby providing a significant reduction in the long term medical risk and financial burden to the cluster headache sufferer.

The single biggest factor/determinant in obtaining the maximum efficacy out of the method of the present invention is hands-on training and coaching of the cluster headache sufferer. If hands-on training is not provided and initial proficiency monitored to ensure that each participant has successfully demonstrated that he or she can follow the procedures correctly prior to sending them home to start routine use of the method of the present invention, the overall results will be diminished.

In a preferred embodiment of the present invention, the demand valve used must provide a delivery pressure of 60+/−5 cm $H_2O$, a flow rate demand mode of 0-160 liters per minute, an inspiration valve crack pressure of 0 to −2 cm $H_2O$ or less, an expiration resistance of 3.8 cm $H_2O$ or less at 11-70 liters per minute and accept a feed or input pressure from an oxygen source of 40 to 60 psi.

If a demand valve does not have sufficiently sensitive expiration pressure levels for the individual patient, a one way T valve adapter typically used in critical care circuits such as but not limited to, that available from Intersurgical Ltd., can be connected to the demand valve output port directly or by means of routinely available connector adapters also available for critical care breathing circuits. Such T valve adapters do not interfere with the inspiration phase of breathing, but they provide lower expiration pressures then the typical medical oxygen resuscitation demand valve. For a cluster headache patient in extreme pain, suffering from anxiety, and trying to concentrate on a specific protocol of breathing vs. random breathing driven by anxiety, easy inspiration and expiration facilitates the method of the present invention.

In cluster headache therapy there is only one user of the system, which is the patient. Therefore, reusable oxygen resuscitation masks usually sold for use with the demand valve in emergency medicine can be repeatedly used by the same cluster headache sufferer for an extended period with routine cleaning using, for example, special wipes or towelettes sold for continuous positive airway pressure or CPAP masks. Such an oxygen resuscitation mask will provide a consistently tight seal around the user's face, assuring inhalation of 100% oxygen without leaks, and will provide sufficient structure and durability to withstand the rough treatment that occurs during a cluster headache attack in terms of the mask being held very tightly by the user. While not intended to be limiting, it has been found that the reusable AMBU® Silicone Facemask with blue cuff designed for use in resuscitation, ventilation and anesthesia is optimum due to the efficacy of its facial seal, comfort, it being made of an unbreakable plastic, its surface being designed for firm gripping with the hand, its availability in several sizes and it being readily cleaned. Disposable anesthesia masks are an alternative, but the model used must also provide a tight seal around the patients face and be easily and firmly gripped by the users hand or the claimed method is reduced in efficacy. Without intending to be self limiting such a disposable mask includes the EcoMask™ II from Intersurgical Ltd.

An alternative to use of a full face mask is the use of a mouthpiece affixed to the demand valve instead of a mask. Many cluster headache sufferers prefer the use of a mouthpiece due to the allodynia that is symptomatic for some cluster headache sufferers where the attack causes the facial area on the hit side to become extremely painful to touch. Use of the mouthpiece requires practice to be effective, and may require nose clips similar to those used by swimmers in order to prevent nasally inhaled air from diluting the 100% oxygen being inhaled through the mouthpiece connected to the demand valve. Without practice to ensure a proper seal around the mouthpiece, the user may inhale air around the mouthpiece if gripped loosely between their teeth while in the midst of a cluster headache while in immense pain and hyperactive. Furthermore, use of a mouthpiece in effect purses the lips which can lead to an incomplete emptying of lungs on expiration which is not desirable from the standpoint of efficacy of the method hereof.

A high pressure compressed gas cylinder of medical oxygen is also required as a source with an output port providing 40-60 psi. These output ports are generally called a quick connect, and in the US is also known to anyone involved in the field as a DISS connection, involving a threaded check-valve connection. In other countries these compressed gas cylinder output port quick connects may employ a bayonet type connection similar to that used on hospital oxygen wall outlets. This range of psi pressure is required to feed a medical demand valve to support the method of the present invention which delivers up to 160 liters per minute flow rate upon inspiration. Therefore, present state of the art liquid oxygen systems cannot be used as they are limited to 15 liters per minute continuous flow and usually short durations of time at that flow rate before the manifold freezes up and malfunctions. Medical oxygen wall outlets in hospitals and other medical facilities or ambulances that deliver 99.5% to 100% medical oxygen at 40 to 60 psi may be used. Oxygen concentrators based on molecular sieve or pressure swing absorption technology cannot be used because their flow rates are under 15 liters per minute continuous flow, and they have the added deficit of providing only 93% oxygen.

Using the method of the present invention, 100% oxygen is only breathed for a maximum of 30 minutes at a time and is more than likely to be breathed for typically 15 to 20 minutes or less at a time with considerable breaks in between breathing room air.

Use of 100% oxygen with a demand valve as described for the method of the present invention is safe. In the U.S., Oxygen USP, readily available from thousands of medical gas filling and distribution facilities or homecare services, and of a purity 99.5 mole percent oxygen or greater, is the least invasive and most cost effective of all cluster headache abortives.

Kafer E. R., "Pulmonary oxygen Toxicity: A Review of the Evidence of Acute and Chronic Toxicity in Man," *Brit J Anaesthesia* 1971, 43, 687-695, showed no toxic effects in normal human subjects within 3 hours of exposure to 100% oxygen. Sackner M. A., Landa J., Hirsch J., Zapata A., "Pulmonary Effects Of Oxygen Breathing. A 6-Hour Study In Normal Men." *Ann Intern Med* (1975 January) 82(1):40-3, reported that 100% oxygen at atmospheric pressure is safe if given for less than 6 hours, with substernal stress occurring as early as 4 hours after the start of oxygen breathing but usually developing between the $12^{th}$ and $15^{th}$ hour.

As Matharu 2003 noted, the great advantage with oxygen for cluster headaches is that it has no established adverse effects. Oxygen can be readily combined with other abortive and preventative medications and procedures with no contraindications. It can be used several times a day as opposed to subcutaneous sumatriptan or nasal zolmitriptan, which can each only be used up to a maximum of two times a day. This is of critical importance due to the large number of cluster headache sufferers, in particular chronic sufferers, who have far more than 2 cluster headache attacks per day, day in and day out, for extended months if not years, in part due to re-attacks which also occur with these triptans just as they do with the most recent update to the standard of care oxygen therapy using 7-15 liters per minute continuous flow and a non-rebreathing mask.

The method of the present invention is used for periods of 15 to 20 minutes or up to a maximum of 30 minutes with intervals breathing normal air in between and is considered very safe.

The U.S. Navy uses 100% oxygen in most tactical jet aircraft breathing systems to simplify the breathing system, to provide an underwater breathing capacity in the event of a crash at sea, and to maximize night vision. (U.S. Naval Flight Surgeon's Manual, Third Edition, 1991, Prepared by Naval Aerospace Medical Institute: p 2-9.) It should also be noted that Naval Aviators, (Navy and Marine Corps air crews) flying tactical fixed-wing aircraft have for many decades breathed 100% oxygen using demand valve-like regulators on all flights from takeoff to touch down on missions averaging more than two hours in duration as well as during long duration missions seven hours or more in length such as extended combat missions and trans-oceanic non-stop flights with no ill-effects or documented medical problems. Moreover, it is also common for pilots to hyperventilate for periods of several minutes at a time during high stress situations such as flights over hostile territory involving air to air and air to ground combat missions and during tactical training missions. According to the US Navy's hyperbaric oxygen therapy Treatment Table 6, the safe-dosing limits for oxygen therapy allow for periods of 30 and 60 minutes breathing 100% oxygen with only 15-minute breaks breathing normal air. (U.S. Naval Flight Surgeon's Manual, Third Edition, 1991, Prepared by Naval Aerospace Medical Institute: p 1-71.) These oxygen exposure tables are conservative and structured to guard against both central nervous system, also known as CNS oxygen toxicity and pulmonary oxygen toxicity, while at pressures equal to depths of 30 to 60 feet or 10 to 20 meters under water, respectively, representing 2 and 3 Bar pressure. It takes 6 to 12 hours breathing 100% oxygen continuously at sea level to encounter symptoms of pulmonary oxygen toxicity, and these symptoms are easily reversed by breathing normal air. Accordingly, the method of the present invention never requires that the cluster headache sufferer use demand valve inhalation of 99.5% to 100% oxygen for more than 30 minutes at a time without a minimum of 15 minutes breathing normal air. This makes the risk of pulmonary oxygen toxicity so extremely low that the method of the present invention will generate no lasting or harmful side effects if performed as recommended.

With a demand valve, the patient controls their intake of oxygen with respiration rate. It is not controlled by the standard of care relatively low fixed continuous flow rate of oxygen entering a non-rebreathing mask determined by an external flow meter affixed to a compressed gas cylinder, or a liquid oxygen system, or an oxygen concentrator. With a demand valve, the cluster headache sufferer is provided with an oxygen source that can deliver far and above their maximum potential inspiratory and tidal volumes needed even if fast hyperventilating due to pain and anxiety or because they are following the method hereof in order to rapidly abort their pain and therefore reduce their level of anxiety.

A demand valve is required in order to enable the method hereof. Without a demand valve, fast and slow hyperventilation as described above is not possible. The use of a current standard of care non-rebreathing mask system with a routinely available medical oxygen flow meter being limited to a maximum oxygen continuous flow rate of 15 l/min or even on some units 25 l/min into such a mask system is insufficient to support fast or slow hyperventilation.

As previously noted, when using a non-rebreathing mask system, key factors in achieving adequate cluster headache therapy include continuous flow oxygen rate, mask volume, reservoir bag volume, ventilatory resistance and tightness of mask fit. The use of a demand valve provides as much oxygen as the cluster headache sufferer can inhale and is not rate limited as is continuous flow by the standard flow meters on a medical oxygen compressed gas cylinder or what can be generated by a liquid oxygen or concentrator system. The mask volume, which in a non-breathing mask involves both the mask and the reservoir bag that is part of the assembly, is not an issue with a demand valve. When the patient inhales, they are opening a valve in the demand valve assembly just in front of the patients full face mask that introduces a high flow rate of oxygen, and when the patient exhales their exhaled gases exit a vent valve within the demand valve. This vent valve, unlike those present on non-rebreathing mask systems, is substantial in construct and within a hard plastic or metal housing and therefore not subject to breakage due to rough physical contact directly or by holding the mask or demand valve hard with the fingers. The availability of a high flow rate of oxygen upon activation of the valve by low inspiration pressure compares to the effort of a cluster headache patient having to forcefully try and inhale or gasp oxygen and/or mixed gases from their non breathing mask reservoir bag, particularly when the flow of oxygen into the non-breathing mask does not match the inspiratory rate and tidal volume of a hyperventilating patient. Finally, a typical non-breathing mask system is disposable and the mask is made of soft pliable plastic. Being intended by design to be used for respiratory therapy of COPD patients, the mask in general is worn by being held in place by a head strap alone which, while it may provide a loose or firm seal against the face, is not a tight seal and is prone to leaks. In the case of its intended respiratory therapy application there is a margin of acceptability for such leaks occurring and a reduction from the optimum 100% oxygen delivery. However, this is not the case in cluster headache therapy with oxygen, where it is critical for effective abortive therapy to achieve as close to 100% oxygen saturation of the blood as possible. The use of mask systems in the method of the present invention which are originally intended for resuscitation, ventilator or anesthesia use must provide a tight face seal and allow itself to be firmly gripped without damage by a cluster headache sufferer during an attack.

The method of the present invention and in the Example that follows, in general significantly reduces abort time and duration of pain for a cluster headache sufferer and reduces or eliminates re-attacks. It can be used an unlimited number of times in a 24 hour period compared to the leading abortive triptans such as injected sumatriptan and inhaled zolmitriptan, which are limited to a recommended 2 doses per day, a critical factor for cluster headache sufferers having numerous cluster headaches or re-attack cluster headaches per day.

The use of oxygen instead of sumatriptan or zolmitriptan can eliminate one potential ingredient from the pharmaceutical cocktail usually taken by cluster headache sufferers which can have cardiac side adverse effects, and provide an abortive method which can be used by pregnant and nursing women, young children or the elderly in whom use of sumatriptan or zolmitriptan is not indicated.

For the individual cluster headache sufferer the method of the present invention can (i) potentially reduce the number and severity of cluster headaches per day and therefore potentially change the nature of the condition in the individual patient; (ii) be used with other abortive and or preventative and or opioid pharmaceuticals, or reduce or eliminate the cluster headache sufferers need for other abortive and or preventative and or opioid medications; (iii) improve the quality of life by reducing abort time and the number of cluster headaches suffered through allowing the patients, for example, to engage in meaningful employment without excess absence and iv) reduce the cost of healthcare to the cluster headache sufferer and insurers who now cover the cost of the prohibitively expensive triptans approved for cluster headache such as subcutaneous sumatriptan injection.

Therefore, use of the method of the present invention, by a cluster headache patient can be a superior alternative to subcutaneous injection of sumatriptan, which as noted by Ekbom 2002, was the abortive method of choice based on the effectiveness of this form of sumatriptan versus the historical and current standard of care for oxygen use of 7 l/min to 12 l/min or even 15 l/min continuous flow with a non-rebreathing mask system.

Because of its safety, oxygen in the method of the present invention can also be as an abortive prior to, during or after surgical or invasive therapeutic procedures for cluster headache such as, but not limited to, occipital nerve stimulation or gamma knife surgery.

In a period of rising healthcare costs, medical insurance companies in general provide minimal if any coverage for the on label and off label abortive medications used for cluster headache including oxygen, subcutaneously injected sumatriptan and inhaled zolmitriptan. The two forms of triptan cited above are noted in the literature to be extremely expensive and within members of the largest cluster headache patient organizations the cost of these triptans, in particular subcutaneously injected sumatriptan, is a particular concern if not financial nightmare. In the period just prior to the filing of this application, cluster headache sufferers reported that medical insurance companies are starting to drop them as clients due to the cost of providing them with this particular drug on an ongoing chronic basis. Hence, there is a need for a low cost and highly effective abortive therapy represented by the method of the present invention that a medical insurance company would be willing to pay for and/or which a cluster headache sufferer could, if dictated by circumstances, afford out of pocket. Medical oxygen, as illustrated by Oxygen USP in the U.S., which is the active drug agent in the present invention, is several factors lower in cost per dose then either injectable sumatriptan or inhaled zolmitriptan.

Example 1

A pilot patient diary study has been and continues to be conducted with consistent and successful results, initially involving several severe chronic cluster headache sufferers 50 years of age or greater, in part selected based on studies in the medical literature reporting that this subgroup has a lower success rate in aborting headaches using oxygen then either episodics or younger chronic sufferers.

Hence, if a method of using oxygen to effectively and consistently abort a cluster headache could be found for this chronic and over 50 years of age patient subgroup, then it was postulated that the same method should provide an equal if not superior rate of success for episodic patients who reportedly already have a higher success rate then this chronic subgroup with current standard of care methods of oxygen delivery such as continuous flow 7-15 l/min and non-rebreathing mask systems.

Participants were provided with the necessary delivery systems and accessories, including standard non-rebreathing mask systems and medical oxygen demand valves historically used in emergency resuscitation having the required specifications, and with a patient diary report form to fill in as they had cluster headaches and attempted aborts with oxygen using the different devices and methods. The initial phase was to establish a baseline using the current standard of care non-rebreathing mask system with a high continuous flow rate of 15 l/min. In the secondary phase, the applicants determined by trial and error which method of demand valve use in the same patients led to the highest percentage of cluster headache aborts and in the shortest period of time. In the tertiary phase the determined method, which is the method of the present invention, was implemented.

The study recorded 27 aborts using the non-rebreathing mask system at 15 l/min continuous flow and 124 aborts using the method of the present invention over a period of months. Use of the method of the present invention resulted in a 95% success rate across the 124 cluster headache attacks of Kip 8 pain level or below, which was significant as chronic cluster headache sufferers over the age of 50, as amply reported in the literature, have a lower rate of success with the standard of care non-rebreathing mask and 7 to 15 l/min continuous flow oxygen therapy then do episodic patients. The high rate of efficacy of the invented demand valve method was coupled with a significant reduction in abort times vs. the standard of care non-rebreathing mask and high standard rate of continuous flow, as illustrated in FIG. 1, which depicts results for two of the pilot study participants.

A positive correlation exists between Kip pain level during therapy and time to abort using the method of the present invention. The data collected using the method hereof indicate that abort times occurring between Kip-4 and Kip-8 will be 5.7 to 12.5 minutes at a 95% confidence level, with all participants achieving successful demand valve abort rates>95% for attacks≦Kip-8. The one Kip 9 cluster headache recorded took 25 minutes to abort. This is significantly less, usually by 50%, than the times required for a complete abort at that pain level using a non-rebreathing mask system with 15 l/min continuous flow oxygen.

A side-by-side video of the same cluster headache sufferer experiencing a Kip 7-8 cluster headache using a standard oxygen non-rebreathing mask system at 15 l/min and the method of the present invention clearly shows the significant difference in abort time and reduction in physical stress and activity during the cluster headache during and after the abort phase. Study participants all of which have experience using sumatriptan injections, felt that the demand valve method more rapidly aborted their cluster headache, and, due to the logarithmically lower cost of oxygen versus sumatriptan injections, was the preferred method of aborting their cluster headache below a Kip 8 pain level.

One participant temporarily reverted to use of a demand valve without the method of the present invention but just breathing as needed or driven by the pain and anxiety of a cluster headache attack for an extended number of cluster headaches, incremental to those counted above using the method of the present invention. The lack of significant benefit compared to the method hereof and increase in the number of cluster headaches which probably largely consisted of re-attacks, as illustrated by FIG. 2, re-confirmed the superiority of the method of the present invention.

The two participants whose data is depicted in FIG. 1 experienced a dramatic reduction in the intensity and frequency of cluster headache attacks, and they were able to significantly reduce their use of sumatriptan injections. One of these two participants suffering from an extreme and extended chronic cluster headache condition lasting many years was using up to 7 sumatriptan injections and 3 morphine injections a day when no more than 2 sumatriptan injections a day are recommended in the suppliers package insert. He had been out of work and on full disability for about 10 years due to the severity of his cluster headache condition and warned by his cardiologist to stop using more than 2 sumatriptan injections per day. The method of the present invention was able to eliminate for a time and then significantly reduce his need for both the abortive sumatriptan injection and opioid morphine for pain management. Remaining attacks (≦Kip-5) now occur at a rate of only 2 or 3 a week, with most coming at night during sleep. This indicates a potential but significant change in the nature of the condition resulting from some mechanism unknown at the present time, where the use of the invention was the only new variable.

All pilot diary study participants concurred that once an attack has reached Kip-9 or Kip-10 on a rapid rise of pain during a "high cycle" period, none of the abortives, including oxygen or subcutaneously injected sumatriptan, will be very effective. The general consensus was that starting early with the demand valve therapy hereof will prevent most of the runaway cluster headache attacks that escalate up to Kip-9 and Kip-10 unless there are other factors present or the cluster headache sufferer is asleep when the attacks starts.

Re-attacks, which are an attack occurring 15 to 45 minutes after a successful abort, are common during the first month after starting the method of the present invention, but can also occur at a later date. They occurred in 1 out of 4 aborts where the Kip pain level is high (7-8) and abort times are less than 15 min. The demand valve therapy was modified to counter the incidence of re-attacks.

The demand valve therapy method of the present invention was safe. There were no adverse effects or symptoms encountered in many months of continuous use during Phases 2 through 4 of the pilot diary study, other than dry mouth due to the dry nature of compressed cylinder medical oxygen that is not humidified prior to inhalation.

In an add-on patient diary study now underway, pulse oximetry and pH testing of saliva are being used to determine if oxygen saturation levels can be used to monitor the efficacy of the method of the present invention, and if oxygen saturation or pH can provide a warning indicator that in vivo conditions indicate a pending cluster headache attack prior to physical symptoms such as pain, aura or shadows. Initial results indicate that minute pulse oximetry and pH changes do provide some measure of warning of an impending cluster headache prior to physical symptoms being felt such as the initiation of pain, and, that coupled with the early use of the method of the present invention can abort a cluster headache in even a shorter time frame then if one were to start use of the method hereof at the onset of physically felt symptoms or after a cluster headache has started.

The number of participants in the diary study is in the process of being expanded, and a larger physician managed cluster headache patient clinical study is being developed involving in-clinic patient screening and training in the use of the method of the present invention and nurse monitored outpatient cluster headache sufferer diary data collection.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of easing the duration of pain experienced by a patient during a cluster headache comprising providing a high pressure source of substantially pure oxygen capable of accepting a pressure input of about 50 psi and of delivering a maximum flow rate of at least about 140 l/m, applying said high pressure source of substantially pure oxygen to said patient in a manner such that inhalation by said patient is substantially limited to inhalation of said substantially pure oxygen using a demand valve having a predetermined manual purge flow rate and a variable output flow rate to the user based on respiratory demands, inhaling said substantially pure oxygen in a manner so as to cause hyperventilation by said patient, and continuing said hyperventilation at least until said patient achieves respiratory alkalosis, hypocapnia hyperoxia and until said pain is terminated.

2. The method of claim 1 wherein said applying step further includes applying a facemask to said patient adapted to limit said inhalation to said substantially pure oxygen or applying a mouthpiece that may require nose clips to said patient adapted to limit said inhalation to substantially pure oxygen.

3. The method of claim 1 wherein said inhaling of said substantially pure oxygen comprises said patient inhaling and exhaling substantially completely for at least three inhalations.

4. The method of claim 3 comprising said patient inhaling and exhaling substantially completely for from three to four inhalations.

5. A method of easing the duration of pain experienced by a patient during a cluster headache comprising providing a high pressure source of substantially pure oxygen, applying said high pressure source of substantially pure oxygen to said patient in a manner such that inhalation by said patient is substantially limited to inhalation of said substantially pure oxygen, inhaling said substantially pure oxygen in a manner so as to cause hyperventilation comprising rapidly hyperventilating at a rate of approximately 50 to 60 breaths per minute by said patient, and continuing said hyperventilation at least until said patient achieves respiratory alkylosis, hypercapnia hyperoxia, and until said pain is terminated.

6. The method of claim 5 wherein said continuing of said hyperventilation is carried out for from one to two minutes, or until the effects of said hyperventilation are felt.

7. The method of claim 5 wherein said continuing of said hyperventilation further includes slowly hyperventilating at a rate of about 30 breaths per minute until pain is terminated completely.

8. The method of claim 7 comprising in the event of a re-attack occurs continuing said slowly hyperventilating at about 30 breaths per minute until pain is terminated completely and then continuing slow hyperventilation for at least one additional minute.

9. The method of claim 8 including subsequently slowing respiration to a normal rate of from about 16 to 18 breaths per minute for a period of up to about 15 minutes if said complete termination of said pain takes place in less than about 10 minutes.

10. The method of claim 8 including subsequently slowing respiration to a normal rate of from about 16 to 18 breaths per minutes for a period of up to about 20 minutes if an additional re-attack occurs.

11. The method of claim 10 including subsequently slowing respiration to a normal rate of from about 16 to 18 breaths per minute for a period of up to about 25 minutes if an additional re-attack occurs.

12. The method of claim 11 including subsequently slowing respiration to a normal rate of from about 16 to 18 breaths per minute for a period of up to about 30 minutes if an additional re-attack occurs.

13. The method of claim 8 including subsequently slowing respiration to a normal rate of from about 16 to 18 breaths per minute for a period of up to about 20 minutes if said complete termination of said pain takes place in between 10 and 15 minutes.

14. The method of claim 8 including subsequently slowing respiration to a normal rate of from about 16 to 18 breaths per minute for a period of up to about 25 minutes if said complete termination of said pain takes place in between 15 and 20 minutes.

15. The method of claim 8 including subsequently slowing respiration to a normal rate of from about 16 to 18 breaths per minute for a period of up to about 30 minutes if said complete termination of said pain takes place in between 20 and 25 minutes.

16. The method of claim 8 including continuing said breathing at said normal rate if re-attacks continue for increasing periods of time of from about 16 to 30 minutes from said inhaling step as needed to prevent or reduce further occurrences of said re-attacks.

17. The method of claim 1 comprising terminating said method after a maximum period of about 30 minutes from said inhaling step in order to breathe normal air for a minimum period of 15 minutes, and subsequently repeating said method.

18. The method of claim 1 repeated as needed.

19. The method of claim 1 carried out in conjunction with the use of one or more co-medications.

20. The method of claim 19 wherein said co-medication is selected from the group consisting of sumitriptan, zoimitriptan, naritriptan, rizatriptan and dihydroergotamine.

21. The method of claim 19 wherein said co-medication comprises a transitional therapeutic comprising prednisone.

22. The method of claim 19 wherein said co-medication comprises a preventive therapeutic selected from the group consisting of verapamil, valproic acid, topiramate, gabapentin, ergot-based medications, indomethicin, methysergide, prednisone and lithium.

23. The method of claim 19 wherein said co-medication comprises an opioid comprising morphine.

24. The method of claim 1 carried out in conjunction with a surgical procedure.

25. The method of claim 1 carried out in conjunction with the use of a pulse oximeter for monitoring oxygen saturation of said patient's blood.

26. The method of claim 1 wherein said demand valve provides a delivery pressure of about 60+/−5 cm of water.

27. The method of claim 1 wherein said demand valve provides a maximum flow rate at least about 160 liters per minute.

28. The method of claim 1 wherein said demand valve provides an inspiration valve crack pressure of from about 0 to −2 cm of water or less to start the inhalation of oxygen.

29. The method of claim 1 wherein said demand valve provides an expiration resistance of about 3.8 cm of water or less at from about 11 to 70 liters per minute and accepts an input pressure from an oxygen source of from about 40 to 60 psi.

30. The method of claim 2 wherein said mask comprises a reusable resuscitation or disposable anesthesia mask with a tight facial seal and which can be held tightly against the face without damaging the integrity of the mask and facial seal or a mouthpiece and nose clips to prevent the inhalation of any room air.

31. The method of claim 2 including using a one-way T valve between said demand valve output port and said mask or mouthpiece.

32. The method of claim 1 wherein said high pressure source of substantially pure oxygen comprises a compressed gas cylinder of oxygen of from between 99.5 and 100% mole concentration oxygen.

33. The method of claim 32 wherein said high pressure source of substantially pure oxygen is capable of accepting a pressure input of about 50 psi and of delivering a maximum flow rate of about 160 l/m.

34. A method of easing the pain experienced by a patient suffering from a cluster headache comprising providing a high-pressure source of pure oxygen capable of accepting a pressure input of about 50 psi and of delivering a maximum flow rate of at least about 140 l/m and a demand valve, inhaling said pure oxygen in a manner so as to cause hyperventilation by said patient, and rapidly changing the rate of said hyperventilation by said patient.

35. A method of easing the pain experienced by a patient suffering from a cluster headache comprising providing a high pressure source of pure oxygen and a demand valve, inhaling said pure oxygen in a manner so as to cause hyperventilation by said patient and rapidly changing the rate of said hyperventilation by said patient including rapidly hyperventilating at a rate of about 50 to 60 breaths per minute and slowly hyperventilating at a rate of from about 30 breaths per minute.

36. The method of claim 34 including applying a facemask to said patient adapted to limit said inhalation to said pure oxygen or applying a mouthpiece that may require nose clips to said patient adapted to limit said inhalation to pure oxygen.

37. The method of claim 34 wherein said high-pressure source of pure oxygen is capable of delivering a maximum flow rate of at least about 160 l/m.

\* \* \* \* \*